United States Patent
Power et al.

(10) Patent No.: US 7,393,660 B2
(45) Date of Patent: Jul. 1, 2008

(54) CC-CHEMOKINE BINDING TICK PROTEINS

(75) Inventors: Christine Power, Thoiry (FR); Amanda Proudfoot, Chens sur Leman (FR); Achim Frauenschuh, Plan-les-Ouates-Geneve (CH)

(73) Assignee: Laboratoires Serono SA, Coinsins (CH)

( * ) Notice: Subject to any disclaimer, the term of this patent is extended or adjusted under 35 U.S.C. 154(b) by 0 days.

(21) Appl. No.: 10/583,218

(22) PCT Filed: Dec. 21, 2004

(86) PCT No.: PCT/EP2004/053638

§ 371 (c)(1),
(2), (4) Date: Feb. 26, 2007

(87) PCT Pub. No.: WO2005/063812

PCT Pub. Date: Jul. 14, 2005

(65) Prior Publication Data

US 2007/0224125 A1   Sep. 27, 2007

(30) Foreign Application Priority Data

Dec. 24, 2003 (EP) ................................. 03104973

(51) Int. Cl.
| | |
|---|---|
| C12N 15/62 | (2006.01) |
| C12N 15/63 | (2006.01) |
| A61K 38/00 | (2006.01) |
| C07K 14/00 | (2006.01) |
| C07H 21/04 | (2006.01) |

(52) U.S. Cl. .................. 435/69.1; 435/71.1; 435/252.3; 435/320.1; 435/69.5; 514/2; 514/12; 530/350; 536/23.4; 536/23.5

(58) Field of Classification Search ........................ None
See application file for complete search history.

(56) References Cited

U.S. PATENT DOCUMENTS 5,849,536 A * 12/1998 Garfinkel et al. ........... 435/69.6

2003/0050244 A1   3/2003 Fuchsberger et al.

FOREIGN PATENT DOCUMENTS

| WO | WO 00/27873 | 5/2000 |
|---|---|---|
| WO | WO 01/78770 A1 | 10/2001 |

OTHER PUBLICATIONS

Database EMBL "Putative 8.9 kDa secreted protein" Oct. 1, 2002, XP002330449, Accession No. Q8MVA1, abstract.
Database EMBL 'Online! "Danio rerio genomic clone DKEY-12P12, genomic survey sequence" Jun. 6, 2002, XP002330450, Accession No. AL737166, abstract.
Database EMBL "Putative 9.4 kDa secreted protein from Ixodes scapularis" Oct. 1, 2002, XP002295520, Accession No. Q8MVA2, abstract.
Hajnicka, V. et al. "Anti-Interleukin-8 activity of tick salivary gland extracts" *Parasite Immunology*, 2001, pp. 483-489, vol. 23, No. 9.
Kocakova, P. et al. "Effect of fast protein liquid chromatography fractionated salivary gland extracts from different ixodid tick species on interleukin-8 binding to its cell receptors" *Folia Parasitologica*, Mar. 2003, pp. 79-84, vol. 50, No. 1.
Valenzuela, J. G. "Exploring the messages of the salivary glands of *ixodes ricinus*" *Am. J. Trop. Med. Hyg.*, 2002, pp. 223-224, vol. 66, No. 3.
Kovar, L. et al. "Salivary gland extract from *Ixodes ricinus* tick modulates the host immune response towards the Th2 cytokine profile" *Parasitol. Res.*, Dec. 2002, pp. 1066-1072, vol. 88, No. 12.
Anguita, J. et al. "Salp15, an *Ixodes scapularis* salivary protein, inhibits $CD4^+$ T cell activation" *Immunity*, Jun. 2002, pp. 849-859, vol. 16, No. 6.

* cited by examiner

*Primary Examiner*—Christine J. Saoud
*Assistant Examiner*—Jon M Lockard
(74) *Attorney, Agent, or Firm*—Saliwanchik, Lloyd & Saliwanchik

(57) ABSTRACT

A novel CC-chemokine binding protein is isolated from the saliva of *Rhipicephalus sanguineus*. Compounds prepared in accordance with the present invention can be used as anti-inflammatory compounds and in the treatment or prevention of CC-chemokine-related diseases.

28 Claims, 7 Drawing Sheets

Figure 3
A)
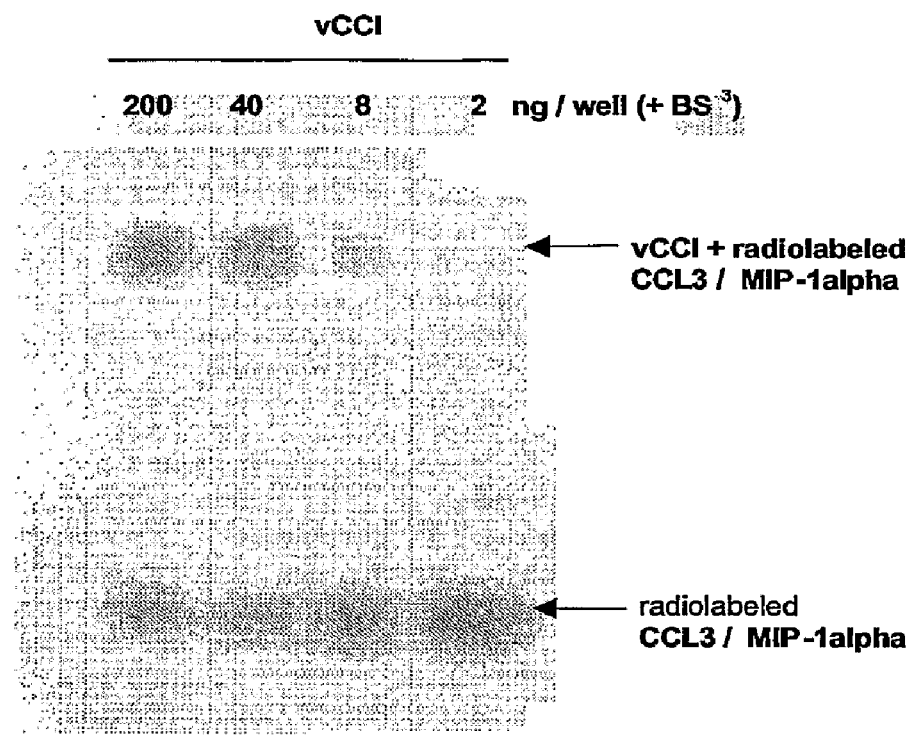
B)
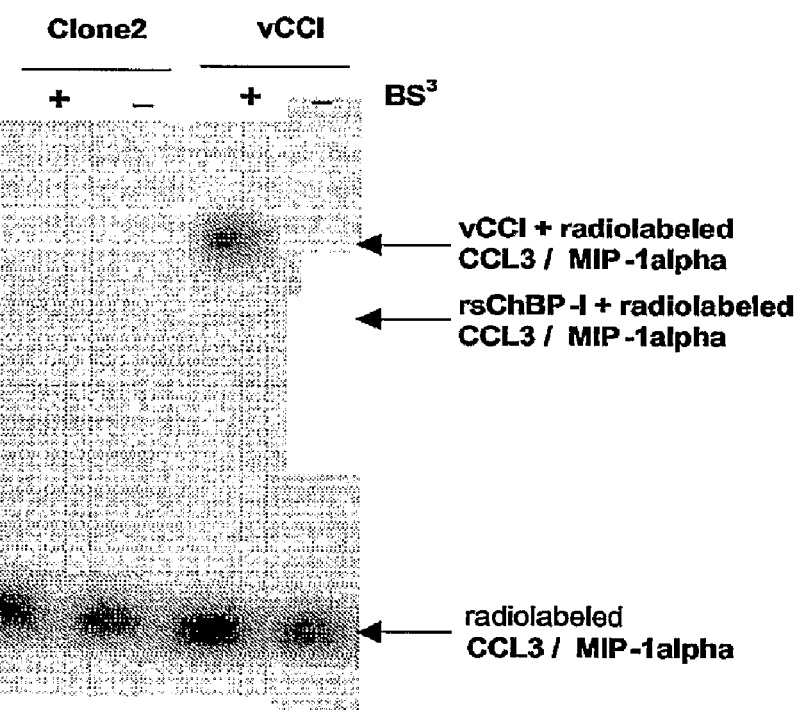

Figure 4

```
  1 GGCCATTACGGCCGGGGGTCCTTGCGCATTCGTGTAGAGCAGCAGCTCAAGTCTTCGAAG

61 ATG CGC ACT TTC GGG GCT TCT CTT TTC GTT
  1 Met Arg Thr Phe Gly Ala Ser Leu Phe Val

91 CTC CTC GCG ATT AGT GTC GCT TAC TGT GAC
 11 Leu Leu Ala Ile Ser Val Ala Tyr Cys Asp

121 GTC CAA GAG CGC GGC CAT ACT TAC GTG ACC
 21 Val Gln Glu Arg Gly His Thr Tyr Val Thr

151 AAA AAT GTG ACG GTC GAA AAC GGT GCC TGC
 31 Lys Asn Val Thr Val Glu Asn Gly Ala Cys

181 GTG TTT GAA CGC AAC GTC ATT CCG GAT GGT
 41 Val Phe Glu Arg Asn Val Ile Pro Asp Gly

210 GAA ACC AAA GCA CTG AAC AGC CCA TGC GTC
 51 Glu Thr Lys Ala Leu Asn Ser Pro Cys Val

241 ATT TCC ACA TGC TAT GCA GCT GAC CGT AAA
 61 Ile Ser Thr Cys Tyr Ala Ala Asp Arg Lys

271 GTG AAC TCG ACT CTC TGC CCG AAC TTC GGA
 71 Val Asn Ser Thr Leu Cys Pro Asn Phe Gly

301 GTT GCG GAG GGC TGC CAT GTG GAG TGG ACC
 81 Val Ala Glu Gly Cys His Val Glu Trp Thr

331 CCC GAT GGT GAA TAC CCG AAC TGC TGC CCG
 91 Pro Asp Gly Glu Tyr Pro Asn Cys Cys Pro

361 AAG CAT GTG TGC CCT ACG GCC CCT GTT ACT
101 Lys His Val Cys Pro Thr Ala Pro Val Thr

391 TCT TAA TCGCATCACATCTGCGAAAATGAA
111 Ser STOP

421 ACGTCGAGACATTCTTCTTTATGCCTTAAGAA ATTAAA CTGCAACGTCCGCAAAAATACA

481 TCCCCGCTTCAAATACGAACAAAATGCAGGATCAAATGCTATTAGGTTTCATGCTGA GTG

541 CAAGCTAA AATAAA CAACTGAATCAGCGTTTAAAAAAAAAAAAAA
```

Figure 5

```
avChBP-I   60 MRALVALACVVVSVAVVIGDIQEHGHSYLKRNVTIENGACIYERNTLPDGETKALHDPCV 239
              MR   A    V+++++V   D+QE GH+Y+ +NVT+ENGAC++ERN +PDGETKAL+  PCV
rsChBP-I   61 MRTFGASLFVLLAISVAY CDVQERGHTYVTKNVTVENGACVFERNVIPDGETKALNSPCV 240
              MR+      + L           H Y    V+++NG C +      + DG++    + PC
isChBP-I    1 MRSIVLWALIALGGVPLLMGAANQSHPYG ---VSFNNGTCTYRNITLRDGDSEPFQYPCE 171 avChBP-I  240 IATCYAERREVNATLCPNFGVDPGCRVQWTPDGIYPECCPKQV CDGTN 383
              I+TCYA  R VN+TLCPNFGV  GC V WTPDG YP CCPK VC
rsChBP-I  241 ISTCYAADRKVNSTLCPNFGVAEGCHVEWTPDGEYPNCCPKHVCPTAPVTS 393
                    C    R +      C         C            +P CC
isChBP-I  172 YWNCNVTARTLTIEGCG -VPRYGSCLYVHNYNFYWPLCCRMSRLC 303
```

CC-CHEMOKINE BINDING TICK PROTEINS

CROSS-REFERENCE TO RELATED APPLICATION

This application is the U.S. national stage application of International Patent Application No. PCT/EP2004/053638, filed Dec. 21, 2004, the disclosure of which is hereby incorporated by reference in its entirety, including all figures, tables and amino acid or nucleic acid sequences.

FIELD OF THE INVENTION

The invention relates to novel antagonists of CC-chemokines and their uses, particularly as anti-inflammatory compounds and in the treatment or prevention of CC-chemokine-related diseases.

BACKGROUND OF THE INVENTION

Chemokines are small, secreted pro-inflammatory proteins, which mediate directional migration of leukocytes from the blood to the site of injury. Depending on the position of the conserved cysteines characterizing this family of proteins, the chemokine family can be divided structurally into C, CC, CXC and $CX_3C$ chemokines that bind to a series of membrane receptors (Baggiolini M et al., 1997; Fernandez E J and Lolis E, 2002). These membrane receptors, all heptahelical G-protein coupled receptors, allow chemokines to exert their biological activity on the target cells, which may present specific combinations of receptors according to their state and/or type. The physiological effects of chemokines result from a complex and integrated system of concurrent interactions: the receptors often have overlapping ligand specificity, so that a single receptor can bind different chemokines. A single chemokine can bind to different receptors as well.

Studies on structure-activity relationships indicate that chemokines have two main sites of interaction with their receptors, the flexible amino-terminal region and the conformationally rigid loop that follows the second Cysteine. Chemokines are thought to dock onto receptors by means of the loop region, and this contact is believed to facilitate the binding of the amino-terminal region that results in receptor activation.

Usually, chemokines are produced at the site of injury and cause leukocyte migration and activation, playing a fundamental role in inflammatory, immune, homeostatic, hematopoietic, and angiogenic processes. Thus, these molecules are considered good target candidates for therapeutic intervention in diseases associated with such processes. The inhibition of chemokines, or of their receptors, can reduce leukocyte maturation, recruitment and activation, as well as other pathological processes related to angiogenesis or arteriosclerosis (Baggiolini M, 2001; Loetscher P and Clark-Lewis I, 2001; Godessart N and Kunkel S L, 2001).

In addition to mutant inhibitory chemokines, antibodies and peptide and small molecule inhibitors blocking the receptors the search for effective chemokine antagonists has also been extended to a series of viruses and other organisms that, when entering into contact with human or mammal hosts, show potent immunomodulatory activities affecting the host. The viral mimicry of cytokines, chemokines, and their receptors may indicate strategies of immune modulation for developing therapeutic products (Alcami A, 2003; Lindow M et al., 2003). Recently, immunomodulatory factors expressed by haematophagous arthropods (such as mosquitoes, sandflies and ticks) have been reviewed (Gillespie, R D et al., 2000; Nuttall P A et al., 2000; Schoeler G B and Wikel S K, 2001).

In particular, the salivary glands of ticks produce a complex mixture of bioactive molecules having, in particular, anti-inflammatory, anti-haemostatic and anti-immune activities. These include bioactive proteins that control histamine, bind immunoglobulins, or inhibit the alternative complement cascade or other proteases.

The effect of these molecules is, probably, to provide a privileged site at the tick-host interface that shelters the tick from the normal innate and acquired host immune mechanisms that combat infections, ensuring successful feeding.

Moreover, tick salivary glands are considered the major route by which tick-borne pathogens enter the host during feeding, since ticks use their salivary glands as a means of concentrating the blood meal by returning the excess fluid and ions back to the host, possibly transmitting pathogens resident in these glands. In fact, tick induced modulation of host immunity is increasingly recognized as an important factor in successful transmission or establishment of tick-borne pathogens.

Immunomodulating activities have been characterized in tick saliva extracts (Alarcon-Chaidez F J et al., 2003; Bergman D K et al., 2000; Anguita J et al., 2002; Gwakisa P et al., 2001; Leboulle G et al., 2002; Kopecky J et al., 1999; Kovar L et al., 2002; Gillespie R D et al., 2001). For example, the saliva from *Rhipicephalus sanguineus* inhibits antigen-stimulated production of immunoglobulins and the expression of IFN-gamma, IL-2 and IL-5 in a dose-dependent manner (Matsumoto K et al., 2003).

CXC-chemokine binding activities, in particular CXCL8/Interleukin 8 binding activities, have been detected (but not characterized in terms of specific protein sequences) in the saliva prepared from several ixodid tick species (*Dermacentor reticulatus, Amblyomma variegatum, Rhipicephalus appendiculatus, Haemaphysalis inermis, Ixodes ricinus*), demonstrating a reduction of the level of detectable IL-8, and inhibiting IL-8 induced chemotaxis of human blood granulocytes. (Hajnicka V et al., 2001; Kocakova P et al. 2003; WO 01/58941; WO 01/48484).

Antigens from *Rhipicephalus sanguineus* elicit potent cell-mediated immune responses in resistant but not in susceptible animals. The saliva introduced during tick infestations reduces the ability of a susceptible animal host to respond to tick antigens that could stimulate a protective immune response. As a consequence, the animals present a disturbed cellular migration to the tick feeding site, which can represent a deficient response against ticks (Ferreira B R et al., 2003).

A homologue of the pro-inflammatory cytokine Macrophage Migration Inhibitory Factor has been detected in the tick, *Amblyomma americanum*. This sequence inhibited the migration of human macrophages in an in vitro functional assay to the same extent as recombinant human MIF (Jaworski D C et al., 2001; WO 01/78770).

Despite the large amount of literature, only a few articles list cDNA sequences identified by random sequencing and differential screens of libraries generated from various tick tissues and/or species. Lists of cDNA sequences have been published for *Amblyomma americanum* and of *Dermacentor andersoni* at different developmental stages (Hill C A and Gutierrez J A, 2000), salivary glands of unfed and fed male *Amblyomma americanum* (Bior A D et al., 2002), male mating *Ixodes scapularis* (Packila M and Guilfoile P G, 2002), salivary glands of *Amblyomma variegatum* (Nene V et al., 2002), of *Rhipicephalus appendiculatus* (Nene V et al., 2004), and of *Ixodes scapularis* (Valenzuela J G et al., 2002a; Francischetti I M et al., 2002).

However, the large majority of these sequences are not characterized biochemically or functionally, and many annotations are entered only on the basis of sequence similarity with known proteins involved in basic cellular functions, such as those previously characterised in tick salivary glands for enzymatic activities or inducing antibody response. In particular, there is no indication of tick proteins acting as CC-chemokine binding proteins.

SUMMARY OF THE INVENTION

Surprisingly, it has been found that the saliva of *Rhipicephalus sanguineus* (dog tick) contains CC-chemokine binding activities. In particular, a novel protein termed rsChBP-1, which binds CC-chemokines and can inhibit the production of lipopolysaccharide (LPS)-induced TNF-α release by monocytes, has now been cloned from a *Rhipicephalus sanguineus* cDNA library, and expressed in mammalian cells. This protein, as well as derivatives, fragments or mimetics thereof, can be used therapeutically, e.g., as modulators of inflammation or as targets for vaccination and for the control of ticks and of tick-borne pathogens.

A first object of the invention relates to a polypeptide comprising the amino acid sequence of rsChBP-1 or of a fragment or analog thereof. Preferred polypeptides of this invention bind a CC-chemokine, and can inhibit the production of lipopolysaccharide (LPS)-induced TNF-α release by monocytes. A specific example of such a polypeptide is rsChBP-1 or a fragment thereof.

A second object of the invention relates to nucleic acid molecules encoding a polypeptide as defined above. Such nucleic acids also include oligonucleotides isolated from them and vectors containing said molecules, in particular expression vectors.

A third object of this invention resides in antibodies that selectively bind the polypeptides as defined above.

A fourth object of this invention relates to host cells and transgenic non-human animals expressing a polypeptide as defined above, as well as methods of producing such cells and transgenic non-human animals.

A fifth object of this invention is a process for preparing a polypeptide as defined above, typically using recombinant technologies.

A sixth object of the invention is a pharmaceutical (including a vaccine or immunogenic) composition comprising a polypeptide or nucleic acid molecule as defined above and a pharmaceutically acceptable carrier or vehicle.

A seventh object of the invention relates to the use of a polypeptide or nucleic acid molecule as defined above as a medicament, in particular for the preparation of a medicament for regulating an immune or inflammatory response in a mammal, as well as to corresponding methods for treatment.

Other features and advantages of the invention will be apparent from the following detailed description.

DESCRIPTION OF THE FIGURES

FIG. 3: detection of CC-chemokine-binding activity in HEK293 culture medium by chemical cross-linking to $^{125}$I-MIP-1alpha. (A) Titration of the positive control (the viral CC-chemokine binding protein vCCI) added to HEK293 culture medium in the indicated amount and in presence of the cross-linking agent ($BS^3$). The free radiolabeled CC-chemokine migrates as a 8 kDa band. The radiolabeled cross-linked complex formed by the CC-chemokine and vCCl migrate as a 35-45 kDa band. (B) Screening of individual clones from the *Rhipicephalus sanguineus* cDNA expression library expressed in HEK293 mammalian cells. The signal observed in the cross-linking experiment with the culture medium of a specific HEK293 clone transformed with this cDNA library (Clone2) is compared the signal obtained with HEK293 culture medium containing vCCl, in presence (lanes +) or in absence (lanes −) of the cross-linking reagent (BS3) The free radiolabeled CC-chemokine and the cross-linked complexes (between the radiolabeled CC-chemokine and the tick or viral CC-chemokine binding protein) are indicated.

FIG. 4: Clone2 DNA sequence (SEQ ID NO: 3), including the ORF encoding for the amino acid sequences of rsChBP-I (SEQ ID NO: 4) The coding portion of the DNA is aligned with the amino acid sequence. The signal sequence (predicted by the algorithm SIGNALJ) is underlined. The predicted polyadenylation sites are boxed.

FIG. 5: alignment of the amino acid sequences of rsChBP-I (SEQ ID NO: 4) with avChBP-I (SEQ ID NO: 8) and isChBP-I (SEQ ID NO: 10), two protein sequences encoded by ORFs identified in non-annotated *Amblyomma variegatum* and *Ixodes scapularis* cDNAs, respectively. The numbering corresponds to the nucleotide position in the respective cDNA sequences Clone2 (SEQ ID NO: 3), BM289643 (SEQ ID NO: 7), and AF483738 (SEQ ID NO: 9). Identical and conserved (indicated with +) residues between rsChBP-I and avChBP-I, and between rsChBP-I and isChBP-I are indicated in bold.

DETAILED DESCRIPTION OF THE INVENTION

Figure 1:
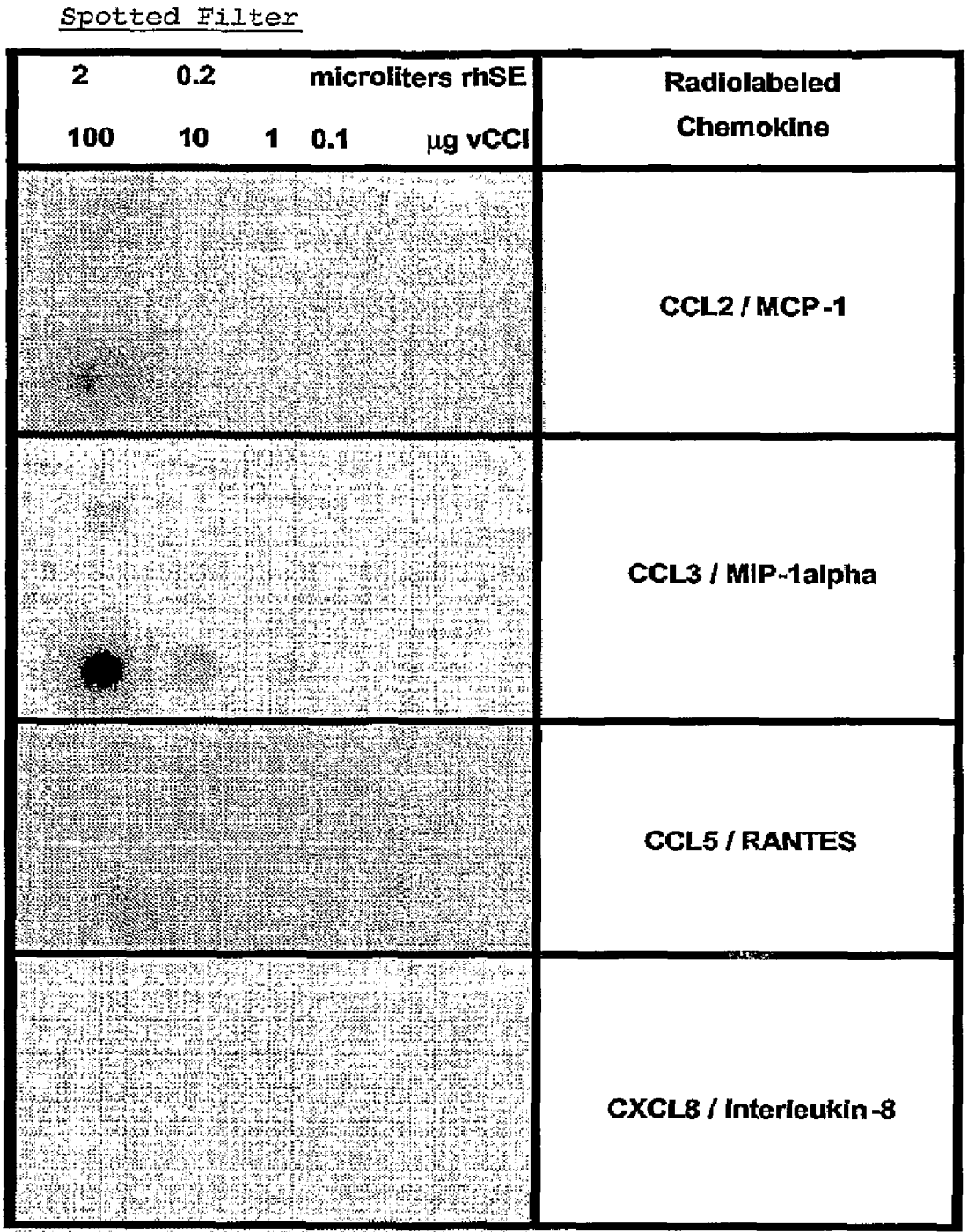
FIG. 1: binding of radiolabelled chemokines to *Rhipicephalus sanguineus* saliva extracts (rsSE) or a CC-chemokine-binding protein from ectromelia virus (vCCI). The extract and the protein were spotted in parallel onto different nitrocellulose filters in the indicated amount (top left cell), then each filter was incubated with the specific radiolabeled chemokine indicated in the column (right).

The present invention provides novel compositions and methods for modulating an inflammatory response. More particularly, the present invention discloses novel proteins having CC-chemokine binding properties that can be used to modulate an inflammatory response. The examples show that this protein, derived from tick saliva, can be expressed and purified in recombinant form, and binds CC-chemokines and inhibits LPS-induced release of TNF-α by monocytes.

A first object of the invention resides in a rsChBP-1 polypeptide, i.e., any polypeptide comprising the amino acid sequence of rsChBP-1 or of a fragment or analog thereof. Preferred polypeptides of this invention bind a CC-chemokine, and inhibit LPS-induced release of TNF-α by monocytes. Particular polypeptides of this invention are selected from the group consisting of:

a) a protein comprising an amino acid sequence of rsChBP-1 (SEQ ID NO: 4);

b) a protein comprising an amino acid sequence of mature rsChBP-1 (SEQ ID NO:6).

c) a protein encoded by a nucleic acid molecule capable of hybridization to a nucleic acid sequence encoding a protein of a) or b) under stringent conditions, said nucleic acid molecule encoding a protein that binds a CC-chemokine and inhibits LPS-induced release of TNF-α by monocytes;

d) a protein at least about 70% identical in amino acid sequence to a protein of a), b), or c), and that binds a CC-chemokine and inhibits LPS-induced release of TNF-α by monocytes;

e) a fragment of a protein of a), b), c), or d), which fragment retains the ability to bind a CC-chemokine and inhibit LPS-induced release of TNF-α by monocytes; and f) a fragment of a protein of a), b), c), d), which fragment has an immunomodulatory activity.

In a still preferred embodiment, the protein is selected from the group consisting of:

a) a protein having an amino acid sequence of rsChBP-1 (SEQ ID NO: 4);

b) a protein having an amino acid sequence of mature rsChBP-1 (SEQ ID NO:6).

c) a fragment of a protein of a) or b), which fragment binds a CC-chemokine and inhibits LPS-induced release of TNF-α by monocytes;

d) a fragment of a protein of a) or b), which fragment has an immunizing activity when administered to a mammal;

e) an active mutant of a protein of a) or b), in which mutant one or more amino acid residues have been added, deleted, or substituted and which said mutant binds a CC-chemokine and inhibits LPS-induced release of TNF-α by monocytes;

f) a fusion protein, which fusion protein comprises a protein of a), b), c), d) or e), operably linked to one or more amino acid sequences chosen amongst the following: an extracellular domain of a membrane-bound protein, an immunoglobulin constant region, a multimerization domain, a signal peptide, an export signal, and a tag sequence, wherein said fusion protein can bind a chemokine and inhibit the LPS-induced release of TNF-α by monocytes.

The polypeptides of the invention can be in a mature form, resulting from one or more post-translational modifications (glycosylation, phosphorylation, modification with endo-/exopeptidases for eliminating the signal peptide, for example) or from the in-frame addition of sequence encoding heterologous sequences (such as tags or domains that improve the detection and/or the purification).

The polypeptides of this invention or their corresponding nucleic acids may be in isolated form (e.g., not in their natural environment), including recombinant or synthetic polypeptides and nucleic acids.

The examples show that rsChBP-1 polypeptides bind CC-chemokines and can be used to inhibit (e.g., reduce) LPS-induced release of TNF-α by monocytes. This characterization was performed by making use of a series of biochemical assays, including the use of radioactive CC-chemokines, or functional assays including cell based assays. As demonstrated in the examples, rsCHBP-1polypeptides bind in particular to CC-chemokines such as CCL3/MIP-1 alpha. rsChBP-1 was shown to inhibit LPS-induced release of TNF-α by monocytes, which indicates an immunomodulatory activity. Such spectrum of activity (i.e., chemokine binding and the inhibition of LPS-induced TNF-α release by monocytes) confers to the rsCHBP-1 polypeptides of this invention a broad range of therapeutic utility, as discussed below.

Within the context of the present invention, a fragment of a polypeptide designates any fragment comprising at least 5, 6, 7, 8, 9 or 10 consecutive amino acid residues of said polypeptide sequence. Particular fragments of this invention comprise 15, 20, 25 or more amino acid residues of a rsCHBP-1protein as disclosed therein. Preferred fragments retain the ability to bind a chemokine, and at least one biological activity of a full-length protein, e.g., an immunogenic activity or an immunomodulatory activity.

In this regard, within the context of the present invention, an "immunomodulatory activity" designates any activity detected in vitro or in vivo that affects the immune response in either a positive or negative manner. Examples of such activities are immunizing activities, immunosuppressive activities, anti-inflammatory activities, pro-/anti-apoptotic activities, or anti-tumoral activities.

Alternatively, the fragment can be identified as providing an immunizing activity when administered to a mammal. These fragments should have appropriate antigenic and immunogenic properties for raising an immune response when needed (for example, against ticks or tick-borne pathogenic organisms). The literature provides many examples on how such functional sequences can be identified as candidate vaccine antigens, and eventually administered with adjuvants and/or cross-linked to a carrier. (Mulenga A et al. 2000; WO 01/80881; WO 03/030931; WO 01/87270). A specific antigen or group of antigens identified in rsChBP-1 can be used for preventing or reducing ectoparasite infection or disease in an animal, so that the immunity of the animal to the ectoparasite is boosted by natural challenge of the animal with the ectoparasite (WO 95/22603). Finally, the fragment can also be used for raising antibodies directed to the entire protein for screening or diagnostic applications.

The properties of rsChBP-1 defined above, and exemplified herein using recombinant variants of this sequence, can be maintained, or even potentiated, in the active mutants. This category of molecules includes natural or synthetic analogs of said sequence, wherein one or more amino acid residues have been added, deleted, or substituted, provided they display the same biological activity characterized in the present invention at comparable or higher levels, as determined by means disclosed in the Examples below.

In particular, the term "active" or "biologically active" means that such alternative compounds should maintain, or even potentiate, the CC-chemokine binding and immunomodulatory properties of rsChBP-1.

Active mutant molecules can be generated by site-directed mutagenesis techniques, combinatorial technologies at the level of encoding DNA sequence (such as DNA shuffling, phage display/selection), or by computer-aided design studies, or any other known technique suitable thereof, which provide a finite set of substantially corresponding mutated or shortened peptides or polypeptides. These alternative molecules can be routinely obtained and tested by one of ordinary skill in the art using the teachings presented in the prior art and in the Examples below.

In accordance with the present invention, preferred changes in these active mutants are commonly known as "conservative" or "safe" substitutions, and involve non-basic residues. Conservative amino acid substitutions are those with amino acids having sufficiently similar chemical properties, in order to preserve the structure and the biological function of the molecule. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provides many models on which the selection of conservative amino acids substitutions can be performed on the basis of statistical and physico-chemical studies on the sequence and/or the structure of natural protein (Rogov S I and Nekrasov A N, 2001). Protein design experiments have shown that the use of specific subsets of amino acids can produce foldable and active proteins, helping in the classification of amino acid "synonymous" substitutions which can be more easily accommodated in the protein structure, and which can be used to detect functional and structural rsCHBP-1 homologs and paralogs (Murphy L R et al., 2000). The synonymous amino acid groups and more preferred synonymous groups for the substitutions are those defined in Table I.

Active mutants of rsChBP-1 may result from sequence alterations reducing the immunogenicity of said CC-chemokine binding protein when administered to a mammal. The literature provides many examples of these sequence alterations that can be designed and introduced at this scope or for other functional optimizations that allow a safe and effective administration of a therapeutic protein, especially when it is a non-human, non-mammalian, or non-natural protein (Schellekens H, 2002). Example of technical approaches for achieving these molecules are directed evolution (Vasserot A P et al., 2003), rational design (Marshall S A et al., 2003), bioinformatics (Gendel S M, 2002), the identification and the neutralization of CD4+ T-cell epitopes (WO 03/104263; WO 03/006047; WO 02/98454; WO 98/52976; WO 01/40281), fusion with other protein sequences (WO 02/79415; WO 94/11028), or conjugation with other compounds (WO 96/40792).

Active rsChBP-1-derived sequences can be natural analogs or orthologs of rsCHBP-1 that may be isolated from, in particular, other tick species, in particular those belonging to the Ixodidae family, and more in particular to the subfamily Rhipicephalinae, to which *Rhipicephalus sanguineus* belongs, as well to other subfamilies like Ixodinae (including *Ixodes scapularis* and *Ixodes ricinus*) or Amblyomminae (including *Amblyomma variegatum* and *Amblyomma americanum*). cDNA sequences encoding polypeptides sharing some homology to rsChBP-1 have been identified from *Amblyomma variegatum* (SEQ ID NO:7) and *Ixodes scapularis* (SEQ ID NO:9). An alignment of the polypeptides encoded by such cDNA sequences are shown in FIG. 5. Alternatively, orthologs may be identified in mammalians, such as man and mouse.

Limited information is available on the genome and the transcriptome of haematophagous arthropods, and is mostly associated with ribosomal and mitochondrial sequences, which were studied to determine the phylogenetic relationships on the basis of their conservation (Murrell A et al., 2001). Tick genomic data are available only in partial and preliminary formats (Ullmann A J et al., 2002), but further analysis of the tick genes encoding CC-chemokine binding proteins can be performed by using genomic DNA that can be extracted from ixodid ticks by applying specific methods and conditions (Hill C A and Gutierrez, J A 2003), in particular for detecting any significant polymorphism in salivary gland proteins, as already demonstrated (Wang H et al., 1999). The genomic and protein sequences of these organisms is important for understanding their physiology and biology, therefore providing information useful for understanding the role of the proteins of the invention in host, parasite, and parasite-born pathogens relationships (Valenzuela J G, 2002b).

The biochemical and physiological characterization of the CC-chemokine binding activities described for protein homologous to rsChBP-1 in the present invention can be performed by applying any of the technologies recently improved for the study of tick and tick-borne pathogens, such as two-dimensional gel electrophoresis (Madden R D et al., 2004) or RNA interference (Aljamali M N et al., 2003). Moreover, further studies can be performed to map the CC-chemokine recognition site on these proteins and the mechanisms of CC-chemokine antagonism (Seet B T et al., 2001; Beck C G et al., 2001; Burns J M et al., 2002; Webb L M et al., 2004) or to identify relevant post-translational modifications (Alarcon-Chaidez F J et al., 2003).

Another object of the invention are fusion proteins comprising a rsChBP-1 polypeptide as defined above operably linked to a heterologous domain, e.g., one or more amino acid sequences which may be chosen amongst the following: an extracellular domain of a membrane-bound protein, immunoglobulin constant regions (Fc region), multimerization domains, export signals, and tag sequences (such as the ones helping the purification by affinity: HA tag, Histidine tag, GST, FLAAG peptides, or MBP).

In the context of a fusion protein, the expression "operably linked" indicates that the rsChBP-1 polypeptide and additional amino acid sequences are associated through peptide linkage(s), either directly or via spacer residues (e.g., a linker). In this manner, the fusion protein can be produced recombinantly, by direct expression in a host cell of a nucleic acid molecule encoding the same, as will be discussed below. Also, if needed, the additional amino acid sequences included in the fusion protein can be eliminated, either at the end of the production/purification process or in vivo, e.g., by means of an appropriate endo-/exopeptidase, as will be discussed below. The heterologous moiety may be operably linked to either the N- or the C-terminal portion of the rsChBP-1 polypeptide.

The design of the moieties and/or linkers, as well methods and strategies for the construction, purification, detection, maturation, and use of fusion proteins are widely discussed in the literature (Nilsson J et al., 1997; "Applications of chimeric genes and hybrid proteins" Methods Enzymol. Vol. 326-328, Academic Press, 2000). In general, the heterologous sequences are intended to provide additional properties without impairing the therapeutic activity of the original protein (CC-chemokine binding, for example) in a significant manner. Examples of such additional properties are an easier purification procedure, a longer lasting half-life in body fluids, an additional binding moiety, the maturation by means of an endoproteolytic digestion, the stability during recombinant production, or extracellular localization. This latter feature is of particular importance for defining a specific group of fusion or chimeric proteins included in the above definition since it allows the polypeptides to be localized in the space where the isolation and purification of these polypeptides is facilitated, and where CC-chemokines are normally active.

The choice of one or more of these sequences to be fused to a rsChBP-1 polypeptide is functional to specific use and/or purification protocol of said protein as recombinant protein. These sequences can be chosen amongst the following three basic groups of heterologous sequences.

A first group of such sequences consists of sequences helping the secretion and the purification of the protein using recombinant DNA technologies, such as a signal peptide and export signals (Rapoport T A et al., 1996), or tag sequences helping the purification by affinity (HA tag, Histidine tag, GST, FLAG, or MBP).

A second group of heterologous sequences is represented by those allowing a better stability and bioactivity of the proteins.

A typical example of a strategy allowing a prolonged half-life of a protein is the fusion with human serum albumin, or with peptides and other modified sequences (e.g. by myristoylation) that allow the binding to circulating human serum albumin, that (Chuang V T et al., 2002; Graslund T et al., 1997; WO 01/77137). Alternatively, the additional sequence may help the targeting to specific localization, such as in the brain (WO 03/32913).

Another way to improve the stability of a recombinant protein when administered to a subject is to generate multimers of the protein by fusing domains isolated from other proteins that allows the formation or dimers, trimers, etc. Examples protein sequences allowing the multimerization of the polypeptides of the Invention are domains isolated from proteins such hCG (WO 97/30161), collagen X (WO 04/33486), C4BP (WO 04/20639), Erb proteins (WO 98/02540), or coiled coil peptides (WO 01/00814).

A well known example of such fusion proteins is represented by the constant/Fc region of human immunoglobulin proteins, allowing the dimerization common to human immunoglobulins. Different strategies for generating fusion protein comprising a therapeutic protein and an immunoglobulin fragment are disclosed in the literature (WO 91/08298; WO 96/08570; WO 93/22332; WO 04/085478; WO 01/03737, WO 02/66514). For example, the nucleic acid sequence encoding the mature RSCHBP-1 can be cloned in an expression vector fused to a nucleic acid sequence encoding the original rsChBP-1 signal sequence (or any other appropriate signal /export sequence) at its 5' end, and the nucleic acid sequence encoding the constant region of human immunoglobulin lambda heavy chain IgG1 (NCBI Acc. No. CAA75302; segment 246-477) at its 3' end. The resulting vector can be used to transform a CHO or HEK293 host cell line and the clones stably expressing and secreting the recombinant fusion protein having rsChBP-1 at the N-terminus and the IgG1 sequence at the C-terminus can be selected. This clone then can be used for scaling up the production and for purifying the recombinant fusion protein from the culture medium. Alternatively, the position of the nucleic acid encoding the constant region of human immunoglobulin lambda heavy chain IgG1 and rsChBP-1 can be inversed, and the resulting protein can be expressed and secreted using still the original signal sequence of rsChBP-1, or any other appropriate signal/export sequence. Using these technology it can be also possible to generate heterodimers if two different constructs expressing one rsChBP-1-Fc fusion protein and the other a different Fc-based fusion protein (for example another CC-chemokine binding protein) are coexpressed in the same host cell (WO 00/18932).

A further group of heterologous sequences is represented by those adding a further functional activity that can synergise or amplify the ones shown by rsChBP-1. These sequences, which are expected to be either isolated from an extracellular domain of a membrane-bound protein (such as a CC-chemokine receptor) or to be present in a secreted protein, can be active as well as CC-chemokine antagonist, and in general should have an immunomodulatory activity.

As mentioned above, the additional sequence included in the fusion proteins may be eliminated, e.g., at the end of the production or purification process, or in vivo, if needed, e.g., by means of an appropriate endo-/exopeptidase. For example, the linker sequence included in the recombinant protein may present a recognition site for an endopeptidase (such as a caspase) that can be used to cleave enzymatically the desired protein from the heterologous sequence either in vivo or in vitro. Alternatively, if the protein sequence to be expressed does not contain a starting methionine (for example, if the sequence encodes for only the mature sequence of the protein, without the signal peptide), a protein of the Invention can be expressed correctly in a host cell with a starting Methionine. This additional amino acid may then be either maintained in the resulting recombinant protein, or eliminated by means of an exopeptidase, such as Methionine Aminopeptidase, according to methods disclosed in the literature (Van Valkenburgh H A and Kahn R A, 2002; Ben-Bassat A, 1991).

Further variants or analogs of the polypeptides of the invention can be obtained in the form of peptide mimetics (also called peptidomimetics), in which the nature of peptide or polypeptide has been chemically modified at the level of amino acid side chains, of amino acid chirality, and/or of the peptide backbone. These alterations are intended to provide antagonists with improved purification, potency and/or pharmacokinetics features. For example, when the peptide is susceptible to cleavage by peptidases following injection into the subject is a problem, replacement of a particularly sensitive peptide bond with a non-cleavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4-dinitrophenyl. Many other modifications providing increased potency, prolonged activity, ease of purification, and/or increased half-life are known in the art (WO 02/10195; Villain M et al., 2001). Preferred alternative, “synonymous” groups for amino acid derivatives included in peptide mimetics are those defined in Table II. By “amino acid derivative” is intended an amino acid or amino acid-like chemical entity other than one of the 20 genetically encoded naturally occurring amino acids. In particular, the amino acid derivative may contain substituted or non-substituted alkyl moieties that can be linear, branched, or cyclic, and may include one or more heteroatoms. The amino acid derivatives can be made de novo or obtained from commercial sources (Calbiochem-Novabiochem AG, Switzerland; Bachem, USA). The techniques for the synthesis and the development of peptide mimetics, as well as non-peptide mimetics, are well known in the art (Hruby V J and Balse P M, 2000; Golebiowski A et al., 2001). Various methodologies for incorporating unnatural amino acids into proteins, using both in vitro and in vivo translation systems, to probe and/or improve protein structure and function are also disclosed in the literature (Dougherty D A, 2000).

As will be discussed below, the polypeptides of the invention may be prepared by any procedure known in the art, including recombinant technologies and chemical synthesis technologies.

A further object of the invention resides in a nucleic acid molecule encoding a polypeptide as defined above, i.e., a polypeptide comprising the amino acid sequence of rsChBP-1 or of a fragment or analog thereof. Particular nucleic acid molecules of this invention are selected from the group consisting of:

a) a nucleic acid molecule encoding a protein comprising an amino acid sequence of rsChBP-1 (SEQ ID NO: 3);

b) a nucleic acid molecule encoding a protein comprising an amino acid sequence of mature rsChBP-1 (SEQ ID NO: 5);

c) a nucleic acid molecule capable of hybridization to a nucleic acid molecule of a) or b) under stringent conditions, and which encodes a protein that binds a CC-chemokine;

d) a nucleic acid molecule encoding a protein at least about 70% identical in amino acid sequence to a protein of a) or b), and that binds a CC-chemokine;

e) a nucleic acid molecule encoding a fragment of a protein encoded by a nucleic acid molecule of a) or b) which fragment binds a CC-chemokine; and f) a degenerate variant of a nucleic acid molecule of a), b), c), d), e).

In particular, the nucleic acid molecule encodes a protein selected from the group consisting of:

a) a protein having an amino acid sequence of rsChBP-1 (SEQ ID NO: 4);

b) a protein having an amino acid sequence of mature rsChBP-1 (SEQ ID NO:6);

c) a fragment of a protein of a) or b), which fragment binds a CC-chemokine;

d) a fragment of a protein of a) or b), which fragment has an immunizing activity when administered to a mammal;

e) an active mutant of a protein of a), b), c), or d), in which mutant one or more amino acid residues have been added, deleted, or substituted and which mutant binds a CC-chemokine; and f) a fusion protein, which fusion protein comprises a protein of a), b), c), d) or e) operably linked to one or more amino acid sequences chosen amongst the following: an extracellular domain of a membrane-bound protein, an immunoglobulin constant region, a multimerization domain, a signal peptide, an export signal, and a tag sequence.

Within the context of the present invention, a "degenerate variant" designates all nucleic acid sequences that, by virtue of the degeneracy of the genetic code, code for the same amino acid sequence as a reference nucleic acid.

Furthermore, the term "nucleic acid molecule" encompasses all different types of nucleic acids, including without limitation deoxyribonucleic acids (e.g., DNA, cDNA, gDNA, synthetic DNA, etc.), ribonucleic acids (e.g., RNA, mRNA, etc.) and peptide nucleic acids (PNA). In a preferred embodiment, the nucleic acid molecule is a DNA molecule, such as a double-stranded DNA molecule, typically a cDNA.

If the main embodiments are directed to the DNA and protein sequences of rsChBP-1 disclosed in the examples, specific embodiments include a series of rsChBP-1-related sequences, such as DNA or RNA sequences capable of hybridizing under moderately stringent conditions (prewashing solution of 5×SSC, 0.5% SDS, 1.0 mM EDTA (pH 8.0) and hybridization conditions of 50° C., 5×SSC, overnight) to the DNA sequences encoding rsChBP-1, and that code for a CC-chemokine binding protein.

For example, the Invention provides the sequence of the cDNA of *Rhipicephalus sanguineus* expressing rsCBP-1 (SEQ ID NO: 3).

In other preferred embodiments the rsChBP-1-related sequences are DNA molecules encoding proteins that are at least about 70%, preferably 80%, and most preferably 90% identical in amino add sequence to rsChBP-1. This value can be calculated with any of the dedicated programs, such as FASTA (Pearson W R, 2000), and, for fragment or partial sequences, it is calculated on that portion of rsChBP-1 that is present in the fragment.

Another preferred embodiment is an oligonucleotide that comprises a fragment of, or that hybridizes specifically to a region of the sequence of a nucleic acid molecule as defined above. Such oligonucleotides typically contain between 5 and 100 nucleotides in length, and can be selected e.g., from the group consisting of oligonucleotides of at least about 20 nucleotides in length, oligonucleotides of at least about 30 nucleotides in length, and oligonucleotides of at least about 50 nucleotides in length. These oligonucleotides can be used for detecting (by PCR or Southern blot, for example) the non-/coding sequences in transcripts encoding rsChBP-1 and related sequences in a sample, or for generating and subcloning recombinant variants of rsChBP-1.

In a further embodiment, the nucleic acid molecules defined above can be comprised in a cloning or expression vector. In this regard, a particular object of this invention resides in an expression vector comprising a promoter operably associated with a nucleic acid molecule as defined above, in particular a tissue specific, constitutive promoter or regulated (e.g., inducible) promoter. The vector may comprise any additional regulatory element, such as a terminator, enhancer, origin of replication, selection marker, etc. The vector may be a plasmid, cosmid, viral vector, phage, artificial chromosome, and the like.

In a particular aspect, this vector can comprise:
a) a DNA of the invention; and
b) an expression cassette;
wherein said DNA (a) is operably associated with a tissue specific, a constitutive, or an inducible promoter included in sequence (b).

Optionally, if the coding nucleic acid (i.e., sequence (a)) does not contain a codon for a starting methionine (for example, if this sequence encodes for only the mature sequence of the protein, without the signal peptide) the vector or expression cassette may also contain an ATG sequence that is cloned in 5' to such sequence so that it can be expressed correctly with a starting Methionine. This additional amino acid may be then either maintained in the resulting recombinant protein, or eliminated by means of an enzyme, such as Methionine Aminopeptidase, according to methods disclosed in the literature (Van Valkenburgh H A and Kahn R A, 2002; Ben-Bassat A, 1991).

This vector may allow the expression of the proteins of the Invention not only in tissue culture but also in vivo, for either experimental or therapeutic reasons. For example, cells overexpressing the protein of the Invention can be transferred (e.g. encapsulated) in an animal model to check the physiological effects of the constant administration of the protein, before applying the cells to humans. Alternatively, the vector can be used for retrovirus-mediated gene transfer, or any other technology allowing the introduction and the expression of a vector or of the isolated DNA coding sequence in animal under the control of an endogenous promoter. This approach allows the generation of transgenic non-human animals in which the proteins of the Invention are expressed constitutively or in a regulated manner (e.g. in specific tissues and/or following the induction with specific compounds). Similar approaches were applied to other non-mammalian chemokine-binding protein, showing various developmental and pathological effects (Jensen K K et al., 2003; Pyo R et al., 2004; Bursill C A et al., 2004).

Another object of the Invention are host cells transformed or transfected with a cloning or expression vector above indicated. These vectors can be used in a process of preparation of the polypeptides of the Invention. In this respect, an object of the invention is a method of preparing a rsChBP-1 polypeptide as defined above, comprising culturing recombinant cells as defined above under conditions allowing or promoting expression and recovering the rsChBP-1 polypeptide. When the vector expresses the polypeptide as a protein secreted in the extracellular space, the protein can be more easily collected and purified from cultured cells in view of further processing.

Many books and reviews provide teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001). In particular, the examples show how, once that the DNA sequence encoding for rsCHBP-1 has been identified by screening the Rhipicephalus sanguineus cDNA library, the ORF can be adapted, modified, and inserted into expression vectors for obtaining the corresponding recombinant protein.

In general, the vectors can be episomal or non-/homologously integrating vectors, which can be introduced in the appropriate host cells by any suitable means (transformation, transfection, conjugation, protoplast fusion, electroporation, calcium phosphate-precipitation, direct microinjection, etc.) to transform them. Factors of importance in selecting a particular plasmid, viral, or retroviral vector include: the ease with which recipient cells that contain the vector, may be recognized and selected from those recipient cells which do not contain the vector; the number of copies of the vector which are desired in a particular host; and whether it is desirable to be able to "shuttle" the vector between host cells of different species. The vectors should allow the expression of the isolated proteins of the invention, or the fusion proteins comprising them in the prokaryotic or Eukaryotic host cell under the control of appropriate transcriptional initiation/termination regulatory sequences, which are chosen to be constitutively active or inducible in said cell. A cell line substantially enriched in such cells can be then isolated to provide a stable cell line For Eukaryotic host cells (e.g. yeasts, insect or mammalian cells), different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells which have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Host cells for recombinant production may be either Prokaryotic or Eukaryotic cells. Particularly suitable Prokaryotic cells include bacteria (such as Bacillus subtilis or E. coli) transformed with a recombinant bacteriophage, plasmid or cosmid DNA expression vectors. Preferred are Eukaryotic host cells, e.g. mammalian cells, such as human, monkey, mouse, and Chinese Hamster Ovary (CHO) cells, because they provide post-translational modifications to protein molecules, including correct folding or glycosylation at correct sites. Alternative Eukaryotic host cells are yeast cells transformed with yeast expression vectors Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognizes leader sequences in cloned mammalian gene products and secretes peptides bearing leader sequences (i.e., pre-peptides).

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

A particularly preferred method of high-yield production of a recombinant polypeptide of the present invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines. In the baculovirus system, the materials for baculovirus/insect cell expression systems are commercially available in kit form from, inter alia, Invitrogen.

Alternatively, the polypeptides of this invention may be prepared by artificial synthesis. In this regard, examples of chemical synthesis technologies are solid phase synthesis and liquid phase synthesis. As a solid phase synthesis, for example, the amino acid corresponding to the carboxy-terminus of the peptide to be synthetised is bound to a support which is insoluble in organic solvents, and by alternate repetition of reactions, one wherein amino acids with their amino groups and side chain functional groups protected with appropriate protective groups are condensed one by one in order from the carboxy-terminus to the amino-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Cl2-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired polypeptide, it is subjected to the de-protection reaction and cut off from the solid support. Such peptide cutting reaction may be carried with hydrogen fluoride or trifluoromethane sulfonic acid for the Boc method, and with TFA for the Fmoc method. Totally synthetic proteins of size comparable to that of rsCHBP-1 are disclosed in the literature (Brown A et al., 1996).

The polypeptides of the present invention can be produced, formulated, administered, or generically used in other alternative forms that can be preferred according to the desired method of use and/or production. The protein of the invention can be post-translationally modified, for example by glycosylation as shown in the examples.

In general the protein of the invention can be provided in the form of active fractions, precursors, salts, derivatives, conjugates or complexes.

As indicated above, the term "active" or "biologically active" means that such alternative compounds should maintain, or even potentiate, the CC-chemokine binding and/or immunomodulatory properties of rsChBP-1.

The term "fraction" refers to any fragment of the polypeptidic chain of the compound itself, alone or in combination with related molecules or residues bound to it, for example residues of sugars or phosphates. Such molecules can result also from other modifications that do not normally alter primary sequence, for example in vitro chemical derivatization of peptides (acetylation or carboxylation), and those made by modifying the protein post-translationally, such as by phosphorylation (introduction of phosphotyrosine, phosphoserine, or phosphothreonine residues) or by glycosylation (by exposing the peptide to enzymes which affect glycosylation e.g., mammalian glycosylating or deglycosylating enzymes) during its synthesis and/or in further processing steps. In particular, rsChBP-1 has been characterized in tick saliva and in both recombinant forms disclosed herein as being more or less heavily glycosylated. This modification may be performed in vitro, by using the appropriate modifying enzyme, or in vitro, by choosing the appropriate host cells for recombinant production.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as used herein refers to derivatives that can be prepared from the functional groups present on the lateral chains of the amino acid moieties or on the amino-/or carboxy-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

The proteins of the Invention can be in the form of active conjugate or complex with a molecule chosen amongst radioactive labels, biotin, fluorescent labels, cytotoxic agents, and drug delivery agents. Useful conjugates or complexes can be generated, using molecules and methods known in the art, for various reasons, for example for allowing the detection of the interaction with CC-chemokines or other proteins (radioactive or fluorescent labels, biotin), therapeutic efficacy (cytotoxic agents), or improving the agents in terms of drug delivery efficacy, such as polyethylene glycol and other natural or synthetic polymers (Harris J M and Chess R B, 2003; Greenwald R B et al., 2003; Pillai O and Panchagnula R, 2001).

These rsChBP-1-derived compounds may be produced following a site-directed modification of an appropriate residue, in an internal or terminal position. Residues can be used for attachment, provided they have a side-chain amenable for polymer attachment (i.e., the side chain of an amino acid bearing a functional group, e.g., lysine, aspartic acid, glutamic acid, cysteine, histidine, etc.). Alternatively, a residue at these sites can be replaced with a different amino acid having a side chain amenable for polymer attachment.

For example, an additional Cysteine allowing direct PEGylation can be added at the N- or C-terminus of the mature protein sequence by recombinant DNA technologies or enzymatically. Alternatively, the Cysteine may be included in the protein by the substitution of a residue, for example in correspondence of a glycosylation site.

Moreover, the side chains of the genetically encoded amino acids can be chemically modified for polymer attachment, or unnatural amino acids with appropriate side chain functional groups can be employed. Polymer attachment may be not only to the side chain of the amino acid naturally occurring in a specific position of the antagonist or to the side chain of a natural or unnatural amino acid that replaces the amino acid naturally occurring in a specific position of the antagonist, but also to a carbohydrate or other moiety that is attached to the side chain of the amino acid at the target position.

Polymers suitable for these purposes are biocompatible, namely, they are non-toxic to biological systems, and many such polymers are known. Such polymers may be hydrophobic or hydrophilic in nature, biodegradable, non-biodegradable, or a combination thereof. These polymers include natural polymers (such as collagen, gelatin, cellulose, hyaluronic acid), as well as synthetic polymers (such as polyesters, polyorthoesters, polyanhydrides). Examples of hydrophobic non-degradable polymers include polydimethyl siloxanes, polyurethanes, polytetrafluoroethylenes, polyethylenes, polyvinyl chlorides, and polymethyl methaerylates. Examples of hydrophilic non-degradable polymers include poly(2-hydroxyethyl methacrylate), polyvinyl alcohol, poly (N-vinyl pyrrolidone), polyalkylenes, polyacrylamide, and copolymers thereof. Preferred polymers comprise as a sequential repeat unit ethylene oxide, such as polyethylene glycol (PEG).

The preferred method of attachment employs a combination of peptide synthesis and chemical ligation. Advantageously, the attachment of a water-soluble polymer will be through a biodegradable linker, especially at the amino-terminal region of a protein. Such modification acts to provide the protein in a precursor (or "pro-drug") form, that, upon degradation of the linker releases the protein without polymer modification.

The present invention also provides antibodies, in particular monoclonal antibodies, that are immunoreactive with the proteins of the invention and that can be raised by immunising an animal with these proteins, which can be purified from natural sources, expressed as recombinant proteins by host cells, or chemically synthesized (as a complete protein or as a peptide mimicking a specific epitope of the protein). These antibodies binding rsChBP-1 and rsChBP-1-derived proteins can be used, for example, in diagnostic applications (e.g. for identifying animals that have been in contact with tick saliva). The generation by immunizing an animal and the engineering of these antibodies can be performed following the teaching in the literature (Kipriyanov S M and Le Gall F, 2004; Holt L J et al., 2003; Presta L, 2003).

The proteins of the invention can be provided in more or less purified forms. The examples show how to clone nucleic acids necessary for expressing recombinant rsChBP-1, how to purify recombinant or natural rsChBP-1 using the affinity for CC-chemokines and chromatographic technologies, and how to select cells properly expressing this protein by means of assays for detecting CC-chemokine binding activities.

In particular, purification of the natural, synthetic or recombinant antagonists of the invention can be carried out by any one of the methods known for this purpose, i.e. any conventional procedure involving extraction, precipitation, chromatography, electrophoresis, or the like. A further purification procedure that may be used in preference for purifying the protein of the invention is affinity chromatography using monoclonal antibodies or affinity groups, which bind the target protein and which are produced and immobilized on a gel matrix contained within a column. Impure preparations containing the proteins are passed through the column. The protein will be bound to the column by heparin or by the specific antibody while the impurities will pass through. After washing, the protein is eluted from the gel by a change in pH or ionic strength. Alternatively, HPLC (High Performance Liquid Chromatography) can be used. The elution can be carried using a water-acetonitrile-based solvent commonly employed for protein purification. Purified preparations of the proteins of the Invention, as used herein, refers to the preparations which are at least 1% (by dry weight), and preferably at least 5%, of said proteins.

Another object of the present invention is a pharmaceutical composition comprising a rsChBP-1 polypeptide as defined above (in the form of proteins and their alternative forms described above) as active ingredient, and a suitable diluent or carrier.

Another object of the present invention is a pharmaceutical composition comprising a nucleic acid molecule encoding a rsChBP-1 polypeptide as defined above, or a corresponding vector or recombinant host cell, and a suitable diluent or carrier.

A further object of this invention relates to the use of a rsChBP-1 polypeptide as defined above, or a nucleic acid encoding the same, for the manufacture of a medicament for use in regulating an immune response in a subject.

These compositions can be used as medicaments, in particular, for regulating an immune or inflammatory response in a mammal, and more particularly as anti-inflammatory compounds.

In general, given the involvement of CC-chemokines in many human and veterinary disorders, the CC-chemokine binding proteins of the invention can used as antagonists of CC-chemokine (such as CCL5/RANTES, CCL3/MIP-1 alpha, or CCL2/MCP-1) for the treatment or prevention of CC-chemokine-related disorders in animals. A non-exhaustive list of CC-chemokine-related disorders includes: inflammatory diseases, autoimmune diseases, immune diseases, infections, allergic diseases, cardiovascular diseases, metabolic diseases, gastrointestinal diseases, neurological diseases, sepsis, diseases related to transplant rejection, or fibrotic diseases. Non-limiting examples of these diseases are the following: arthritis, rheumatoid arthritis (RA), psoriatic arthritis, psoriasis, rheumatoid arthritis, restenosis, sepsis, osteoarthritis, systemic lupus erythematosus (SLE), systemic sclerosis, scleroderma, polymyositis, glomerulonephritis, fibrosis, allergic or hypersensitivity diseases, dermatitis, asthma, chronic obstructive pulmonary disease (COPD), inflammatory bowel disease (IBD), Crohn's diseases, fibromas, ulcerative colitis, multiple sclerosis, septic shock, viral infection, cancer, endometriosis, transplantation, graft-versus-host disease (GVHD) cardiac and renal reperfusion injury, and atherosclerosis.

The proteins of the invention, or specific fragments, can be used as active ingredients in the manufacture of pharmaceutical compositions for regulating an immune or inflammatory response in a mammal, for example of anti-inflammatory compositions. Alternatively, the proteins of the invention, or specific fragments, can be used as active ingredients in the manufacture of pharmaceutical compositions for the vaccination of a mammal against parasites, virus, or bacteria. The process for the preparation of such pharmaceutical compositions comprises combining rsChBP-1 together with a pharmaceutically acceptable diluent or carrier.

A pharmaceutical composition containing a protein of the invention as active ingredient can be used for binding a CC-chemokine in vivo, blocking the binding of a CC-chemokine to a corresponding cell surface receptor and consequently producing a potentially therapeutic effect, such as an anti-inflammatory effect. A pharmaceutical composition containing a protein of the invention as active ingredient, can be used also for binding to CC-chemokine analogues present in viruses, bacteria, or parasites to block entry of said virus, bacteria, or parasite into cells. Pharmaceutical compositions for vaccination of a mammal against a parasite, a virus or a bacteria, can comprise a fragment of the protein of the invention as active ingredient. The compositions above indicated can further comprise an additional immunosuppressant or anti-inflammatory substance.

The pharmaceutical compositions may contain, in combination with the proteins of the invention as active ingredient, suitable pharmaceutically acceptable diluents, carriers, biologically compatible vehicles and additives which are suitable for administration to an animal (for example, physiological saline solution) and eventually comprising auxiliaries (like excipients, stabilizers, or adjuvants) which facilitate the processing of the active compounds into preparations which can be used pharmaceutically. The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich G D, 2001; Cleland J L et al., 2001).

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soybean oil, mineral oil, sesame oil).

Any accepted mode of administration can be used and determined by those skilled in the art to establish the desired blood levels of the active ingredients. For example, administration may be by various parenteral routes such as subcutaneous, intravenous, intradermal, intramuscular, intraperitoneal, intranasal, transdermal, rectal, oral, or buccal routes. The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight per day. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

Another aspect of the invention is the use of a protein encoded by a DNA of the Invention as a medicament, in particular in the preparation of a composition for regulating an immune or inflammatory response in a mammal.

Further aspects of the Invention are methods for immunising an animal against a blood-feeding ectoparasite, or for regulating an immune or inflammatory response in an animal in need thereof, comprising administering to said animal with a protein of the Invention said animal for a time and under conditions sufficient to regulate said immune response.

Another object of the invention is a method for treating or preventing CC-chemokine-related diseases comprising the administration of an effective amount of the compounds of the present invention.

An "effective amount" refers to an amount of the active ingredients that is sufficient to affect the course and the severity of the disease, leading to the reduction or remission of such pathology. The effective amount will depend on the route of administration and the condition of the patient.

The wording "CC-chemokine-related diseases" indicate any disease due to an excessive or uncontrolled CC-chemokine production, leading to a massive monocyte/macrophage/neutrophil/T-cell infiltration, and wherein the administration of rsChBP-1 may provide a beneficial effect. A non-exhaustive list of such chronic, acute, or inherited diseases is provided above.

The therapeutic applications of the CC-chemokine antagonists of the invention and of the related reagents can be evaluated (in terms or safety, pharmacokinetics and efficacy) by the means of the in vivo or in vitro assays making use of mammalian cells, tissues and models (Coleman R et al., 2001; Li A, 2001; Methods Mol. Biol vol. 138, "Chemokines Protocols", edited by Proudfoot A et al., Humana Press Inc., 2000; Methods Enzymol, vol. 287 and 288, Academic Press, 1997). A non-limiting list of assays includes: calcium mobilisation, degranulation, upregulation of pro-inflammatory cytokines, upregulation of proteases, inhibition of cellular recruitment in vitro and in vivo.

A further object of the invention are test kits containing any of the compound disclosed in association to the CC-chemokine binding proteins of the invention. For example, a kit for detecting a CC-chemokine or an analogue, a CC-chemokine binding protein or a receptor, the interaction of CC-chemokine and a CC-chemokine binding protein, or antagonists or agonists of said interaction, comprising a detecting reagent and at least a compound selected from the group consisting of:
  a) A nucleic acid molecule (e.g., a DNA);
  b) An oligonucleotide;
  c) A protein; and
  d) An antibody;
derived from the CC-chemokine binding protein of the Invention.

These kits can be used in methods applicable in vitro or in vivo in which a sample is contacted by one of these compound, which can be labeled or immobilized on a solid support.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the Figures specified here below.

EXAMPLES

Example 1

Biochemical Characterization of Chemokine-Binding Activities in the Saliva of *Rhipicephalus sanguineus* (Dog Tick)

The saliva of the tick *Rhipicephalus sanguineus* has been already used to identify molecules having immunomodulating activities (Matsumoto K et al., J Vet Med Sci 2003; Matsumoto K et al., 2001; Ferreira B R and Silva J S, 1998) but not binding or modulating activities directed specifically to CC-chemokines.

Crude *Rhipicephalus sanguineus* tick saliva was obtained according to the protocol as published (Ferreira B R and Silva J S, 1998). Aliquots of *Rhipicephalus sanguineus* saliva extracts (rsSE) were tested using different assays including, as negative control, Bovine Serum Albumin (BSA) and, as positive control, an ectromelia virus protein (called vCCl or p35) binding specifically CC-chemokines (Smith V P and Alcami A, 2000; Alcami A, 2003), in order to compare binding specificity and dose-response effects.

In a first assay, different amounts of rsSE and of vCCl were spotted onto nitrocellulose filters in parallel, each of them exposed to a different radiolabeled, recombinant CC-chemokine (CCL/MCP-1, CCL3/MIP-1alpha, and CCL5/RANTES) or CXC-chemokine (CCL8/Interleukin 8). While no BSA binding was detected with any radiolabeled chemokine, a CC-chemokine specific binding activity, comparable to the one detected using vCCl, was also detected on filters incubated with any of the CC-chemokines. At the same time, no binding was observed on both rsSE and vCCl spotted filters when incubated with radiolabeled CXCL/Interleukin-8 (FIG. 1).

In a second assay, rhSE and vCCl were challenged with specific chemokine/chemokine receptor pairs using the Scintillation Proximity Assay (SPA), a bead-based technology allowing to measure molecular interactions with great precision. In particular, a specific SPA was designed for detecting molecules interfering with the chemokine/chemokine receptor interaction (Alouani S, 2000). Wheat germ agglutinin SPA beads were coated with cell membranes isolated from stably transfected CHO cells expressing a specific chemokine receptor (such as CCR1 or CXCR2) and then incubated with the radiolabeled chemokine alone, in combination with the natural chemokine, or in combination with different amounts of rhSE.

Figure 2:
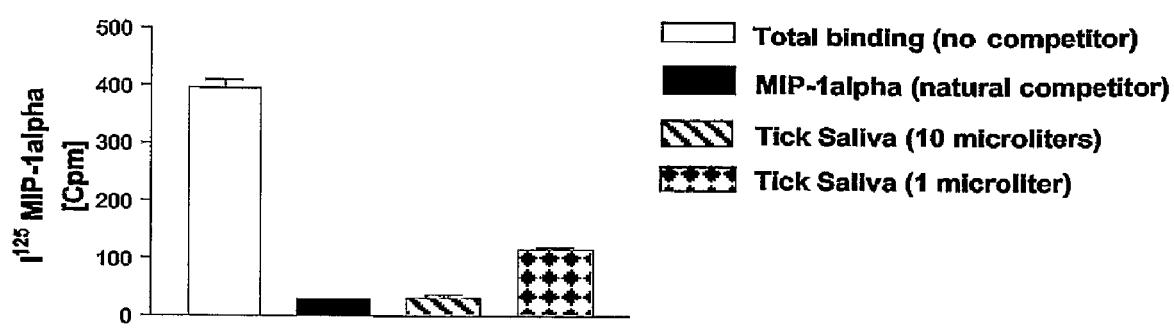
FIG. 2: biochemical characterization of CC-chemokine-binding activities in the saliva of *Rhipicephalus sanguineus* using a Scintillation Proximity Assay (SPA). The interaction between radiolabelled CCL/MIP-1alpha and CCR1 immobilized on SPA beads was measured without a competitor, with the natural competitor (MIP-1alpha), or with two amounts of tick saliva protein extract. A similar profile was obtained using the same SPA beads and radiolabeled or unlabeled CCL5/RANTES.

This assay showed that the interaction between CC-chemokines, in particular for the ones binding CCR1 (CCL3/MIP-1alpha and CCL5/RANTES) is competed by rhSE in a dose dependent manner (FIG. 2). The same assay, when applied for the CXCR2/CXCL8 pair, confirmed the negative results obtained with the spotted nitrocellulose filters.

A cross-inhibition SPA experiment was performed by using a CXC-chemokine competitor in presence of a radiolabeled CC-chemokine/chemokine receptor pair and vice versa. The CXC-chemokine (CXCL8/Interleukin 8) does not interfere with the rhSE-mediated inhibition of the CCR1/CCR5 binding of a radiolabeled CC-chemokine (CCL3/MIP-1alpha), confirming the specificity of the binding activity in rhSE for CC-chemokines.

Similar CC-chemokine binding activities were also detected with the assays above described in the saliva of *Ambylomma* tick species, indicating that other tick species express CC-chemokine binding activities.

Moreover, cross-linking experiments using rhSE and radiolabeled chemokines showed that the cross-linking reagent (bis(sulphosuccinimidyl)suberate or BS3) generates a molecular species having an apparent total molecular weight of approximately 20 kDa when separated in SDS-PAGE. Since radiolabeled CCL3/MIP-1alpha migrates in SDS-PAGE as 8 kDa protein, rhSE expresses a CC-chemokine binding protein having a molecular weight in the range of 10-15 kDa.

Example 2

Construction and Screening of a *Rhipicephalus sanguineus* cDNA Library and Characterization of rsChBP-I The CC-chemokine binding activity identified in rhSE was then identified at the level of DNA/protein sequence by generating a cDNA library from *Rhipicephalus sanguineus* salivary glands that was then used to produce pools of mammalian cells expressing such cDNAs as proteins secreted in the culture medium.

By comparing the CC-chemokine binding activity detected in culture medium obtained from vCCl expressing cells (or culture medium "spiked" with recombinant vCCl) as a control, these media were then screened using a radiolabeled CC-chemokine (CCL3/MIP-1alpha), starting from pools of cells and progressively reducing to single cDNA clones.

Human embryonic kidney cells 293 (HEK293 cells; ATCC Cat. No. CRC-1573; maintained in DMEM-F12 Nut Mix, 10% heat-inactivated fetal calf serum, 2 mM L-Glutamine, 100 units/ml penicillin-streptomycin solution) were chosen to express both vCCl and the cDNA library from *Rhipicephalus sanguineus* salivary glands.

Culture medium from HEK293 cells were obtained from cells grown in complete medium. After three days in culture, the conditioned culture medium was harvested, centrifuged to remove cell debris and the supernatant used in a crosslinking or SPA assay.

The crosslinking experiments were performed on samples transferred to a flat-bottom 96-well plate (Costar). The radiolabeled CC-chemokine (50 µl of 0.23 nM $^{125}$I-CCL3/MIP-1alpha) was added to each sample, which was then incubated with shaking for 2 hours at room temperature. A 25 µl aliquot from each well was then transferred to another well to containing 0.5 µl of 50 mM BS3 (crosslinking reagent) and further incubated for 2 hours with shaking. After this time 5 µl of 10× sample buffer (0.1 M Tris-HCl pH 8 and 10 mM DTT) were added to each well to stop the crosslinking reaction. The samples were then boiled for 5 minutes and electrophoresed on a 10% Bis-Tris SDS-polyacrylamide gel (Invitrogen NuPAGE, catalog no. NP0301BOX). After electrophoresis the gel was sealed in Saranwrap™ and exposed to a K-type storage phosphor-imaging screen (Biorad) for 8 hours. Imaging screens were scanned at a resolution of 100 um using a Biorad Personal FX phosphoimager The *Rhipicephalus sanguineus* cDNA library was constructed into pTriplEx2 (BD Biosciences Clontech). Salivary glands were harvested from 100 adult *Rhipicephalus sanguineus* and were immediately stored in ice-cold RNAlater solution (Ambion) until further use. Total RNA was extracted using the TRIzol method (Gibco-BRL) according to the manufacturer's instructions, and the cDNA library was constructed using the SMART cDNA library construction kit (Clontech) and cDNA size-fractionated with a ChromaSpin 400 column (Clontech) according to the manufacturers instructions. The size of the cloned cDNA inserts ranged from about 0.6 kb to 1.5 in 80% of the inserts.

Both DNA sequence (SEQ ID NO:1) encoding for control protein vCCl (SEQ ID NO:2) and the cDNA library from *Rhipicephalus sanguineus* salivary glands were subcloned in the pEXP-lib expression plasmid (BD Biosciences Clontech).

The pEXP-Lib vector contains an expression cassette comprising the human cytomegalovirus (CMV) major immediate early promoter/enhancer followed by a multiple cloning site including Sfi IA and Sfi IB sites (two distinct Sfi I sites that differ in their interpalindromic sequences), by an internal ribosome entry site (IRES) of the encephalomyocarditis virus (ECMV), which permits the translation of two open reading frames from one messenger RNA, by the gene encoding puromycin resistance (puromycin-N-acetyl-transferase), and by the polyadenylation signal of the bovine growth hormone. Ribosomes can enter the bicistronic mRNA either at the 5' end to translate the gene of interest in the proper orientation, or at the ECMV IRES to translate the antibiotic resistance marker. When culturing pEXP-Lib Vector transformed cells, the antibiotic exerts selective pressure on the whole expression cassette; thus, a high dose of antibiotic (10-100 µg/ml of puromycin) select only cells expressing a high level of the gene of interest. This selective pressure also ensures that the expression of the gene of interest will be stable over time in culture.

HEK293 cells were transfected with pEXP-Lib plasmids using a GenePorter2 transfection kit (Gene Therapy Systems) according to the manufacturer's protocol.

The vCCl protein sequence (SEQ ID NO:2) was detected in the culture medium of HEK cells mixed with a $^{125}$I-labelled CCL3/MIP-1alpha using BS3 (a cross-linking reagent) either when the medium was "spiked" with recombinant vCCl and when the medium was from vCCl-expressing HEK293. The addition of the cross-linking reagent generates a protein complex containing the radiolabeled CC-chemokine complex that is separated in SDS-PAGE as a band migrating at ~40-45 kDa. This cross-linking method is very sensible since even complexes in the nanogram weight range can be detected (FIG. 3A).

When this method is applied to HEK293 cells transformed with a *Rhipicephalus sanguineus* cDNA library, it was possible to screen, starting from pools of cells, a single clone (Clone2) expressing a CC-chemokine binding protein (identified as rsChBP-I) that forms a complex with radiolabeled CCL3/MIP-1alpha migrating in SDS-PAGE as a band of approx. 20 kDa (FIG. 3B). This band, which is centered in the same weight range of the native CC-chemokine binding activity detected in the tick saliva, appears as a smear probably due to the presence of isoforms having different levels of glycosylation.

The cDNA encoding for rsChBP-I expressed by Clone2 was sequenced. This 585 bp long cDNA (SEQ ID NO: 3) contains an Open Reading Frame (ORF) encoding for a 111 amino acid (SEQ ID NO: 4), potentially secreted and having no significant homology with any known CC-chemokine binding protein (FIG. 4). Given the molecular weight, this rsChBP-I sequence should correspond at least one of the CC-chemokine binding activities identified in the tick saliva.

The sequence of rsChBP-I has certain similarities to a protein sequence encoded by an ORF in a non-characterized 515 bp long cDNA (GenBank Acc. No. BM289643; SEQ ID NO: 7) isolated from salivary glands of *Amblyomma variegatum* (Nene V et al., 2002) and by an ORF in a non-characterized 396 bp long cDNA (GenBank Acc. No. AF483738; SEQ ID NO: 9) isolated from salivary glands of *Ixodes scapularis* (Valenzuela J G et al., 2002). This two additional protein sequences (identified avChBP-I and isChBP-I; FIG. 5) contains several conserved cysteines (residues 40, 59, 64, 76, 86, 98, and 99 in rsChBP-I), and are homologous to the screened *Rhipicephalus sanguineus* sequence also in terms of protein length (around 110 amino acids).

Figure 7:
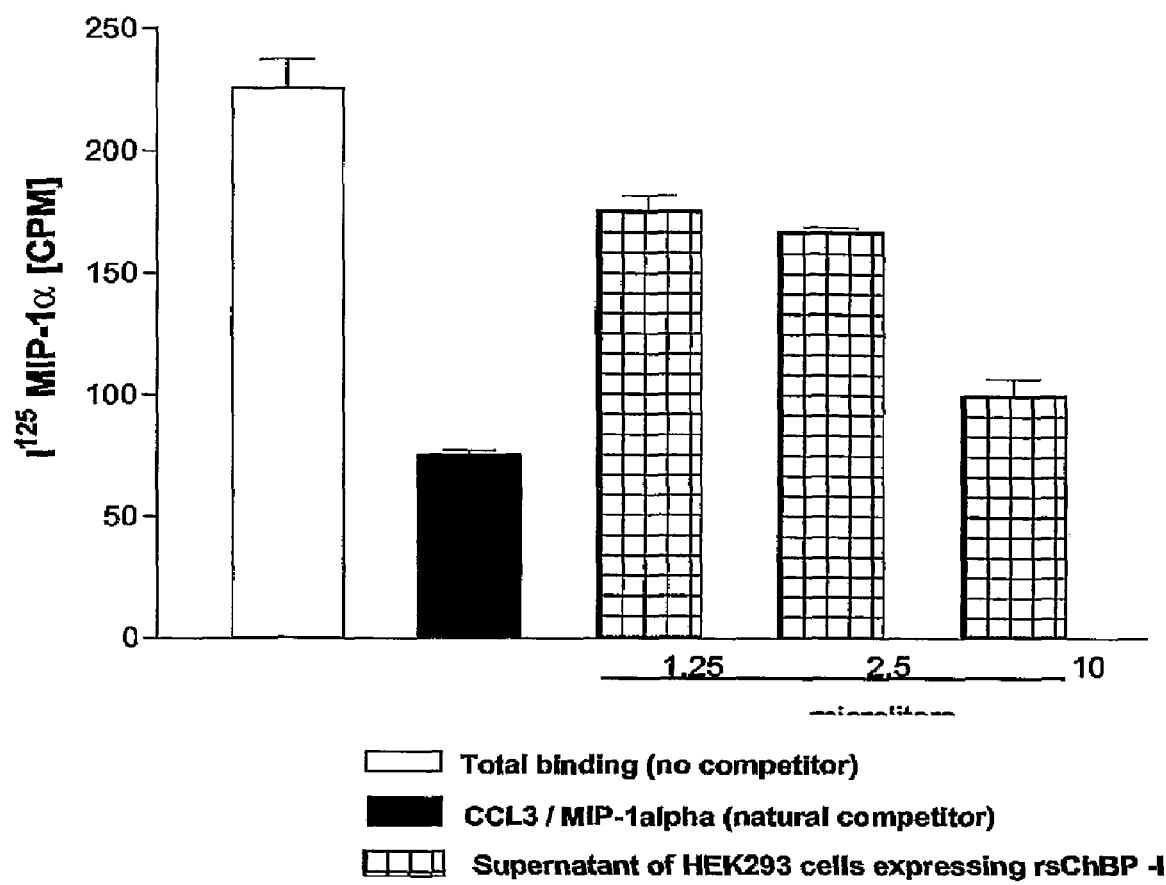
FIG. 7: CC-chemokine binding activity of recombinant rsChBP-I expressed in HEK293 culture medium. The interaction between radiolabeled CCL3/MIP-1alpha and CCR1 is measured in a Scintillation Proximity Assay performed with or without the natural competitor, or with an increasing amount of culture medium from HEK293 cells expressing rsChBP-I added to the sample.

The CC-chemokine binding properties of the protein encoded by Clone2 were also tested using the SPA-based approach. As shown for the rsSE (FIG. 2), the SPA signal measured in presence of rsChBP-I is inversely proportional to the amount of HEK293-Clone2 culture medium added to the sample, with a dose-dependent inhibition effect on the binding of radiolabeled CCL3/MIP-1alpha to the SPA beads (FIG. 7).

Therefore, it can be concluded that rsChBP-I, avChBP-I, and isChBP-I may be members of a novel family of proteins having CC-chemokine binding properties.

Example 3

Functional Assays Characterizing rsChBP-1

LPS-Induced TNF-α Release by Monocytes

The biological activity of rsChBP-1 was determined by an assay which tested for the ability of rsChBP-1 protein to inhibit LPS-induced TNF-α release by monocytes.

Figure 6:
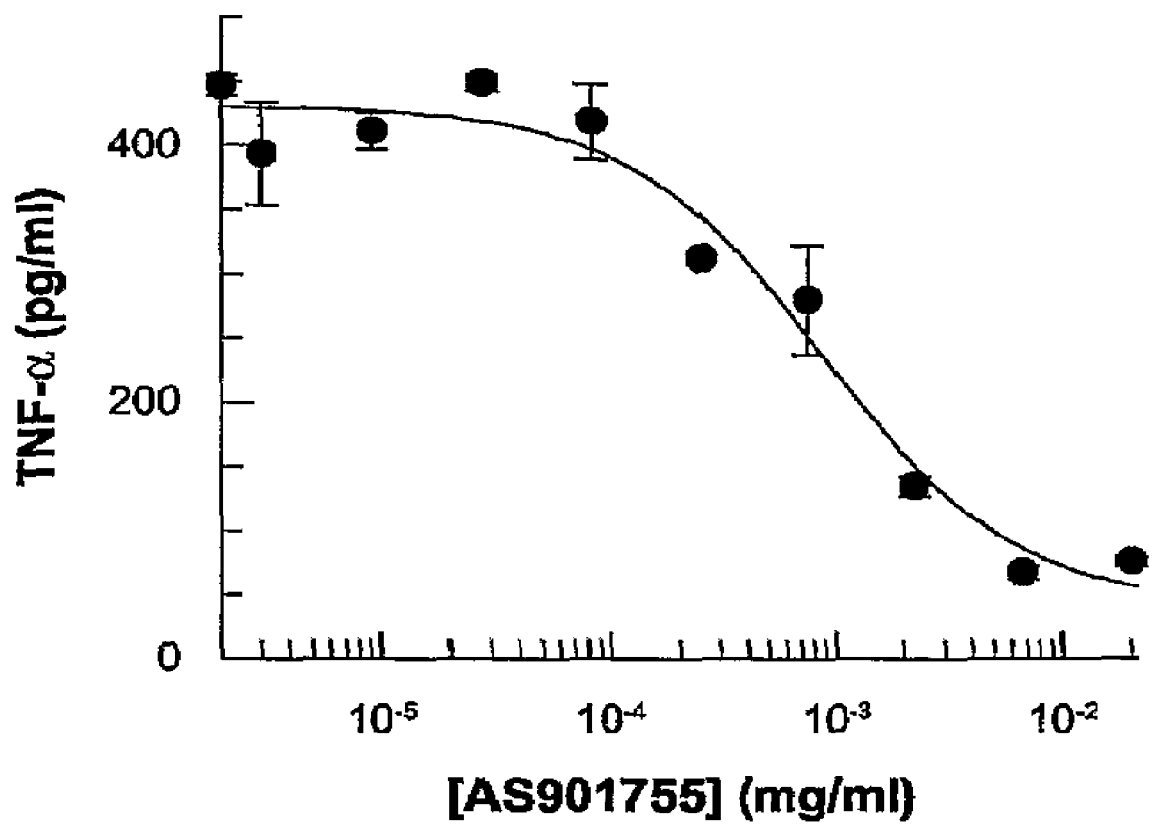
FIG. 6: Inhibition of LPS-induced TNF-α induction by monocytes-waiting for scientists description

A monocyte cell line, THP-1, was seeded in T225 ml flasks at a density of $2.5 \times 10^5$ cells/ml in growth medium (RPMI medium containing 10% FCS, 1% penicillin-streptomycin). The cells were then differentiated by culturing them in 80 nM Vitamin D3 for 72 h. The differentiated cells were plated in 96-well plates at a density of $10^5$ differentiated cells per well, in 150 µl of growth medium. Serial dilutions of rsCHBP-1 protein (as shown in FIG. 6) were added to the cells, in a 50 µl volume, and the cells were left for 24 h in the medium containing the test proteins. The following day, LPS was added to the cells to a final concentration of 2.5 ng/ml, for 3.5 h. The plates were centrifuged, the medium removed from the wells, and stored at −80° C. before performing the ELISA.

The TNF-α ELISA was performed according to the manufacturer's directions, using the DuoSet human TNF-α ELISA kit (R & D Systems DY210). 96-well ELISA plates were coated with 100 µl capture antibody, diluted to 4 µg/ml in PBS. Plates were left overnight at room temperature for this incubation step. The capture antibody solution was removed, and the wells saturated with 200 µl 10% FCS in PBS, for 45 min at room temperature. The plates were washed twice in wash buffer (PBS containing 0.05% Tween-20). 100 µl of medium harvested from the cells was added per well and allowed to incubate for 2.5 h at room temperature. Dilutions of recombinant human TNF-α were used as a standard, according to the instructions from the kit. After incubation, the plates were washed 3× in wash buffer, and incubated with 300 ng/ml detection antibody diluted in PBS, 0.05% Tween-20. The plates were washed 4× in wash buffer and then incubated for 30 min at room temperature with 100 µl per well streptavidin-HRP (diluted 1:10,000 in PBS 0.05% Tween-20). After the incubation, the plates were washed 3× in wash buffer and incubated for 10 min in the dark in 100 µl/well Supersignal ELISA Pico-Chemiluminescent substrate (Pierce, 37070), according to manufacturer's instructions. The level of chemiluminescence was measured in an Ascent Luminoskan luminometer.

Results: rsChBP-1 was shown to inhibit LPS-induced release of TNF-α by a monocytic cell line, indicating that rsChBP-1 can function as an immunomodulatory agent. The $IC_{50}$ obtained in this assay for rsChBP-1 protein was 1 µg/ml.

TABLE I

| Amino Acid | Synonymous Group | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE II

| Amino Acid | Synonymous Group |
|---|---|
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-Met, D-Ile, Orn D-Orn |
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenyl-proline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S--Me-Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |

TABLE II-continued

| Amino Acid | Synonymous Group |
|---|---|
| Glu | D-Glu, D-Asp, Asp, Asn, D-Asn, Gln, D-Gln |
| Met | D-Met, S-Me--Cys, Ile, D-Ile, Leu, D-Leu, Val, D-Val |

REFERENCES

Alarcon-Chaidez F J et al., Parasite Immunol, 25:69-77, 2003.
Alcami A, Nat Rev Immunol, 3:36-50, 2003.
Aljamali M N et al., Insect Mol Biol, 12:299-305, 2003.
Alouani S, Methods Mol Biol, 138:135-141, 2000.
Anguita J et al., Immunity, 16:849-859, 2002.
Baggiolini M et al., Annu Rev Immunol, 15:675-705, 1997.
Baggiolini M, J Intern Med, 250:91-104, 2001.
Beck C G et al., J Biol Chem, 276:43270-43276, 2001.
Ben-Bassat A, Bioprocess Technol., 12:147-159, 1991
Bergman D K et al., J Parasitol, 86:516-525, 2000.
Bior A D et al., Insect Biochem Mol Biol, 32:645-655, 2002.
Brown A et al., J Pept Sci, 2:40-46, 1996.
Burns J M et al., J Biol Chem., 277:2785-2789, 2002.
Bursill C A et al., Circulation, 110:2460-2466, 2004.
Chuang V T et al., Pharm Res., 19:569-577, 2002.
Cleland J L et al., Curr Opin Biotechnol, 12:212-9, 2001.
Coleman R et al., Drug Discov Today, 6:1116-1126, 2001.
Dougherty D A, Curr Opin Chem Biol, 4:645-52, 2000.
Fernandez E J and Lolis E, Annu Rev Pharmacol Toxicol, 42:469-499, 2002
Ferreira B R and Silva J S, Vet Immunol Immunopathol, 64:279-293, 1998.
Ferreira B R et al., Vet Parasitol, 115:35-48, 2003.
Francischetti I M et al., Blood, 99: 3602-3612, 2002.
Gendel S M, Ann NY Acad SCI, 964:87-98, 2002.
Gillespie R D et al., Parasite Immunol, 22:319-331, 2000.
Gillespie R D et al., J Immunol, 166:4319-4326, 2001.
Godessart N and Kunkel S L, Curr Opin Immunol, 13:670-675, 2001.
Golebiowski A et al., Curr Opin Drug Discov Devel, 4:428-34, 2001.
Graslund T et al., Protein Expr Purif., 9:125-132, 1997.
Greenwald R B et al., Adv Drug Deliv Rev, 55:217-250, 2003.
Gwakisa P et al., Vet Parasitol, 99:53-61, 2001.
Hajnicka V et al., Parasite Immunol, 23:483-489, 2001.
Harris J M and Chess R B, Nat Rev Drug Discov, 2:214-221, 2003.
Hill C A and Gutierrez J A, Microb Comp Genomics, 5:89-101, 2000.
Hill C A and Gutierrez J A, Med Vet Entomol, 17:224-227, 2003.
Holt L J et al., Trends Biotechnol, 21:484-490, 2003.
Hruby V J and Balse P M, Curr Med Chem, 7:945-970, 2000.
Kipriyanov S M and Le Gall F, Mol Biotechnol, 26:39-60, 2004.
Kocakova P et al., Folia Parasitol, 50:79-84, 2003.
Kopecky J et al., Parasite Immunol, 21:351-356, 1999.
Kovar L et al., Parasitol Res, 88:1066-1072, 2002.
Jaworski D C et al., Insect Mol Biol, 10:323-331, 2001.
Jensen K K et al., J Virol, 77:624-630, 2003.
Leboulle G et al., J Biol Chem, 277:10083-10089, 2002.
Li A, Drug Discov Today, 6:357-366, 2001.
Lindow M et al., Trends Pharm Sci, 24:126-130, 2003.
Loetscher P and Clark-Lewis I, J Leukoc Biol, 69:881-884, 2001.
Luo B and Prestwich G D, Exp Opin Ther Patents, 11:1395-1410, 2001.
Madden R D et al., Exp Appl Acarol, 32:77-87, 2004.
Marshall S A et al., Drug Disc Today, 8:212-221, 2003.
Matsumoto K et al., J Vet Med Sci, 65:137-140, 2003.
Mulenga A et al., Microbes Infect, 2:1353-1361, 2000.
Murphy L R et al., Protein Eng, 13:149-152, 2000.
Murrell A et al., Mol Phylogenet Evol, 21:244-258, 2001.
Nene V et al., Int J Parasitol, 32:1447-1456, 2002.
Nene V, et al., Insect Biochem Mol Biol., 34:1117-1128, 2004.
Nilsson J et al., Protein Expr Purif, 11:1-16, 1997.
Nuttall P A et al., J Mol Microbiol Biotechnol, 2:381-386, 2000.
Packila M and Guilfoile P G, Exp Appl Acarol, 27:151-160, 2003.
Pearson W R, Methods Mol Biol., 132:185-219, 2000.
Pillai O and Panchagnula R, Cur Opin Chem Biol, 5:447-451, 2001.
Presta L, Curr Opin Struct Biol, 13:519-525, 2003.
Pyo R et al., Am J Pathol, 164:2289-2297, 2004.
Rapoport T A et al., Annu Rev Biochem., 65:271-303, 1996.
Rogov S I and Nekrasov A N, Protein Eng, 14:459-463, 2001.
Schellekens H, Nat Rev Drug Disc, 1:457-462, 2002.
Schoeler G B et and Wikel S K, Ann Trop Med Parasitol, 95:755-771, 2001.
Seet B T et al., Proc Natl Acad Sci USA, 98:9008-9013, 2001.
Ullmann A J et al., Exp Appl Acarol, 28:107-126, 2002.
Valenzuela J G et al., J Exp Biol, 205:2843-2864, 2002a.
Valenzuela J G, Am J Trop Med Hyg, 66:223-224, 2002b.
Vasserot A P et al., Drug Disc Today, 8:118-126, 2003.
Van Valkenburgh H A and Kahn R A, Methods Enzymol., 344:186-193, 2002.
Villain M et al., Chem Biol, 8:673-679, 2001.
Wang H et al., Exp Appl Acarol 1999, 23:969-975, 1999.
Webb L M et al., FASEB J, 18:571-573, 2004.

The invention claimed is:

1. A composition of matter comprising:
   a) an isolated polypeptide comprising:
      i) SEQ ID NO: 4;
      ii) SEQ ID NO: 6; or
      iii) a fusion protein comprising SEQ ID NO: 4 or SEQ ID NO: 6 fused to a heterologous sequence selected from: an extracellular domain of a membrane-bound protein, an immunoglobulin constant region, a multimerization domain, a heterodimeric protein hormone, a signal peptide, an export signal, or a tag sequence;
   b) an isolated polynucleotide:
      A) encoding a polypeptide, said polypeptide comprising:
         i) SEQ ID NO: 4;
         ii) SEQ ID NO: 6; or
         iii) a fusion protein comprising SEQ ID NO: 4 or SEQ ID NO: 6 fused to a heterologous sequence selected from: an extracellular domain of a membrane-bound protein, an immunoglobulin constant region, a multimerization domain, a heterodimeric protein hormone, a signal peptide, an export signal, or a tag sequence;
      B) comprising SEQ ID NO: 3; or
      C) comprising SEQ ID NO: 5;
   c) a vector comprising a polynucleotide:
      A) encoding a polypeptide comprising:
         i) SEQ ID NO: 4;
         ii) SEQ ID NO: 6; or
         iii) a fusion protein comprising SEQ ID NO: 4 or SEQ ID NO: 6 fused to a heterologous sequence selected from: an extracellular domain of a membrane-bound protein, an immunoglobulin constant region, a multimerization domain, a heterodimeric protein hormone, a signal peptide, an export signal, or a tag sequence;
B) comprising SEQ ID NO: 3; or
C) comprising SEQ ID NO: 5; or
d) an isolated host cell transformed or transfected with an expression vector comprising a polynucleotide:
A) encoding a polypeptide comprising:
i) SEQ ID NO: 4;
ii) SEQ ID NO: 6; or
iii) a fusion protein comprising SEQ ID NO: 4 or SEQ ID NO: 6 fused to a heterologous sequence selected from: an extracellular domain of a membrane-bound protein, an immunoglobulin constant region, a multimerization domain, a heterodimeric protein hormone, a signal peptide, an export signal, or a tag sequence;
B) comprising SEQ ID NO: 3; or
C) comprising SEQ ID NO: 5.

2. The composition of matter according to claim 1, wherein said composition of matter is a polypeptide that is post-translationally modified.

3. The composition of matter according to claim 2, wherein said composition of matter is a polypeptide that is glycosylated.

4. The composition of matter according to claim 1, wherein said composition of matter is a polypeptide that is PEGylated.

5. The composition of matter according to claim 1, wherein said composition of matter is an isolated polypeptide comprising SEQ ID NO: 4.

6. The composition of matter according to claim 1, wherein said composition of matter is an isolated polypeptide comprising SEQ ID NO: 6.

7. The composition of matter according to claim 1, wherein said composition of matter is an isolated polypeptide comprising a fusion protein comprising SEQ ID NO: 4 or SEQ ID NO: 6 fused to a heterologous sequence selected from: an extracellular domain of a membrane-bound protein, an immunoglobulin constant region, a multimerization domain, a heterodimeric protein hormone, a signal peptide, an export signal, or a tag sequence.

8. The composition of matter according to claim 1, wherein said composition of matter is an isolated polynucleotide encoding a polypeptide comprising SEQ ID NO: 4.

9. The composition of matter according to claim 1, wherein said composition of matter is an isolated polynucleotide encoding a polypeptide comprising SEQ ID NO: 6.

10. The composition of matter according to claim 1, wherein said composition of matter is an isolated polynucleotide encoding a polypeptide comprising a fusion protein comprising SEQ ID NO: 4 or SEQ ID NO: 6 fused to a heterologous sequence selected from: an extracellular domain of a membrane-bound protein, an immunoglobulin constant region, a multimerization domain, a heterodimeric protein hormone, a signal peptide, an export signal, or a tag sequence.

11. The composition of matter according to claim 1, wherein said composition of matter is an isolated polynucleotide comprising SEQ ID NO: 3.

12. The composition of matter according to claim 1, wherein said composition of matter is an isolated polynucleotide comprising SEQ ID NO: 5.

13. The composition of matter according to claim 1, wherein said composition of matter is a vector comprising a polynucleotide, said polynucleotide encoding a polypeptide comprising SEQ ID NO: 4.

14. The composition of matter according to claim 1, wherein said composition of matter is a vector comprising a polynucleotide, said polynucleotide encoding a polypeptide comprising SEQ ID NO: 6.

15. The composition of matter according to claim 1, wherein said composition of matter is a vector comprising a polynucleotide, said polynucleotide encoding a polypeptide comprising a fusion protein comprising SEQ ID NO: 4 or SEQ ID NO: 6 fused to a heterologous sequence selected from: an extracellular domain of a membrane-bound protein, an immunoglobulin constant region, a multimerization domain, a heterodimeric protein hormone, a signal peptide, an export signal, or a tag sequence.

16. The composition of matter according to claim 1, wherein said composition of matter is a vector comprising SEQ ID NO: 3.

17. The composition of matter according to claim 1, wherein said composition of matter is a vector comprising SEQ ID NO: 5.

18. The composition of matter according to claim 1, wherein said composition of matter is an isolated host cell transformed or transfected with an expression vector comprising a polynucleotide encoding SEQ ID NO: 4.

19. The composition of matter according to claim 1, wherein said composition of matter is an isolated host cell transformed or transfected with an expression vector comprising a polynucleotide encoding SEQ ID NO: 6.

20. The composition of matter according to claim 1, wherein said composition of matter is an isolated host cell transformed or transfected with an expression vector comprising a polynucleotide encoding a polypeptide comprising a fusion protein comprising SEQ ID NO: 4 or SEQ ID NO: 6 fused to a heterologous sequence selected from: an extracellular domain of a membrane-bound protein, an immunoglobulin constant region, a multimerization domain, a heterodimeric protein hormone, a signal peptide, an export signal, or a tag sequence.

21. The composition of matter according to claim 1, wherein said composition of matter is an isolated host cell transformed or transfected with an expression vector comprising SEQ ID NO: 3.

22. The composition of matter according to claim 1, wherein said composition of matter is an isolated host cell transformed or transfected with an expression vector comprising SEQ ID NO: 5.

23. A process for preparing a polypeptide comprising culturing a transformed or transfected host cell under conditions allowing or promoting expression of a polypeptide, said host cell comprising:
a) a polynucleotide encoding a polypeptide selected from:
i) SEQ ID NO: 4;
ii) SEQ ID NO: 6;
iii) a fusion protein comprising SEQ ID NO: 4 or SEQ ID NO: 6 fused to a heterologous sequence selected from: an extracellular domain of a membrane-bound protein, an immunoglobulin constant region, a multimerization domain, a heterodimeric protein hormone, a signal peptide, an export signal, or a tag sequence;
b) a polynucleotide comprising SEQ ID NO: 3; or
c) a polynucleotide comprising SEQ ID NO: 5.

24. The process according to claim 23, further comprising purifying the polypeptide.

25. The process according to claim 24, further comprising formulating the polypeptide into a composition.

26. A method of inhibiting TNF-α release by monocytes comprising contacting monocytes with a composition comprising a carrier and a polypeptide comprising SEQ ID NO: 4 or SEQ ID NO: 6.

27. The method according to claim 26, wherein said polypeptide is SEQ ID NO: 6.

28. The method according to claim 26, wherein said polypeptide comprises SEQ ID NO: 4.

* * * * *

SEQUENCE LISTING

<160> NUMBER OF SEQ ID NOS: 10

<210> SEQ ID NO 1
<211> LENGTH: 744
<212> TYPE: DNA
<213> ORGANISM: ectromelia virus

<400> SEQUENCE: 1

```
atgaaacaat atatcgtcct ggcatgcata tgcctggcgg cagctgctat ccctaccagt    60
cttcagcaat cattcgcatc ctcgtgtacg gaagaagaaa acaaccatca tatgggaatc   120
gatgttatta tcaaagtcac caagcaagac caaacaccga ctaatgataa gatttgtcaa   180
tcagtaaccg aagttacaga gtctgaagac gatggggtat ccgaagaagt cgtaaaagga   240
gatcccacca cttattacac tgtcgtcggt ggaggtctga aatgaactt tggattcacc    300 aaatgtcctc agattaaatc catctcagaa tccgctgatg gaaacacagt gaatgctcgg   360
ttgtctagcg tctctccaat gtacggcatt gaatctccag ccatcactca tgaagaagct   420
cttgctatga tcaacgactg tgcggtgtct atcaatatca aatgtagtga agaagagaaa   480
gacagcaaca tcaagaccca tccagtactc gggtctaaca tctctcataa gaaagtgagg   540
tacgaagata tcatcggttc aacgatcgtc gatataaaat gtgtcaagga tctagagttt   600
agcgttcgta tcggagacat gtgcaaggaa gcatctgaac ttgaagtcaa ggatggattc   660
aagtatatcg acggatcggt atctgaaggt gcaaccgatg atacttcact catcgattca   720
acaaaactca aagcgtgtgt ctga                                          744

<210> SEQ ID NO 2
<211> LENGTH: 247
<212> TYPE: PRT
<213> ORGANISM: ectromelia virus

<400> SEQUENCE: 2

Met Lys Gln Tyr Ile Val Leu Ala Cys Ile Cys Leu Ala Ala Ala
1               5                   10                  15

Ile Pro Thr Ser Leu Gln Gln Ser Phe Ala Ser Cys Thr Glu Glu
                20                  25                  30

Glu Asn Asn His His Met Gly Ile Asp Val Ile Ile Lys Val Thr Lys
                35                  40                  45

Gln Asp Gln Thr Pro Thr Asn Asp Lys Ile Cys Gln Ser Val Thr Glu
    50                  55                  60

Val Thr Glu Ser Glu Asp Asp Gly Val Ser Glu Glu Val Val Lys Gly
65                  70                  75                  80

Asp Pro Thr Thr Tyr Tyr Thr Val Val Gly Gly Leu Arg Met Asn
                85                  90                  95

Phe Gly Phe Thr Lys Cys Pro Gln Ile Lys Ser Ile Ser Glu Ser Ala
                100                 105                 110

Asp Gly Asn Thr Val Asn Ala Arg Leu Ser Ser Val Ser Pro Met Tyr
            115                 120                 125

Gly Ile Glu Ser Pro Ala Ile Thr His Glu Glu Ala Leu Ala Met Ile
        130                 135                 140

Asn Asp Cys Ala Val Ser Ile Asn Ile Lys Cys Ser Glu Glu Glu Lys
145                 150                 155                 160

Asp Ser Asn Ile Lys Thr His Pro Val Leu Gly Ser Asn Ile Ser His
                165                 170                 175

Lys Lys Val Arg Tyr Glu Asp Ile Ile Gly Ser Thr Ile Val Asp Ile
                180                 185                 190

Lys Cys Val Lys Asp Leu Glu Phe Ser Val Arg Ile Gly Asp Met Cys
            195                 200                 205

Lys Glu Ala Ser Glu Leu Glu Val Lys Asp Gly Phe Lys Tyr Ile Asp
        210                 215                 220

Gly Ser Val Ser Glu Gly Ala Thr Asp Asp Thr Ser Leu Ile Asp Ser
225                 230                 235                 240
```

Thr Lys Leu Lys Ala Cys Val
            245

<210> SEQ ID NO 3
<211> LENGTH: 585
<212> TYPE: DNA
<213> ORGANISM: Rhipicephalus sanguineus

<400> SEQUENCE: 3

| | | | | | |
|---|---|---|---|---|---|
| ggccattacg | gccggggtc | cttgcgcatt | cgtgtagagc | agcagctcaa | gtcttcgaag | 60 |
| atgcgcactt | tcggggcttc | tcttttcgtt | ctcctcgcga | ttagtgtcgc | ttactgtgac | 120 |
| gtccaagagc | gcggccatac | ttacgtgacc | aaaaatgtga | cggtcgaaaa | cggtgcctgc | 180 |
| gtgtttgaac | gcaacgtcat | tccggatggt | gaaaccaaag | cactgaacag | cccatgcgtc | 240 |
| atttccacat | gctatgcagc | tgaccgtaaa | gtgaactcga | ctctctgccc | gaacttcgga | 300 |
| gttgcgagg | gctgccatgt | ggagtggacc | cccgatggtg | aatacccgaa | ctgctgcccg | 360 |
| aagcatgtgt | gccctacggc | cctgttact | tcttaatcgc | atcacatctg | cgaaaatgaa | 420 |
| acgtcgagac | attcttcttt | atgccttaag | aaattaaact | gcaacgtccg | caaaaataca | 480 |
| tccccgcttc | aaatacgaac | aaaatgcagg | atcaaatgct | attaggtttc | atgctgagtg | 540 |
| caagctaaaa | taacaactg | aatcagcgtt | taaaaaaaaa | aaaaa | | 585 |

<210> SEQ ID NO 4
<211> LENGTH: 111
<212> TYPE: PRT
<213> ORGANISM: Rhipicephalus sanguineus

<400> SEQUENCE: 4

Met Arg Thr Phe Gly Ala Ser Leu Phe Val Leu Leu Ala Ile Ser Val
1               5                   10                  15

Ala Tyr Cys Asp Val Gln Glu Arg Gly His Thr Tyr Val Thr Lys Asn
            20                  25                  30

Val Thr Val Glu Asn Gly Ala Cys Val Phe Glu Arg Asn Val Ile Pro
        35                  40                  45

Asp Gly Glu Thr Lys Ala Leu Asn Ser Pro Cys Val Ile Ser Thr Cys
    50                  55                  60

Tyr Ala Ala Asp Arg Lys Val Asn Ser Thr Leu Cys Pro Asn Phe Gly
65                  70                  75                  80

Val Ala Glu Gly Cys His Val Glu Trp Thr Pro Asp Gly Glu Tyr Pro
                85                  90                  95

Asn Cys Cys Pro Lys His Val Cys Pro Thr Ala Pro Val Thr Ser
            100                 105                 110

<210> SEQ ID NO 5
<211> LENGTH: 420
<212> TYPE: DNA
<213> ORGANISM: Rhipicephalus sanguineus

<400> SEQUENCE: 5

| | | | | | |
|---|---|---|---|---|---|
| gacgtccaag | agcgcggcca | tacttacgtg | accaaaaatg | tgacggtcga | aaacggtgcc | 60 |
| tgcgtgtttg | aacgcaacgt | cattccggat | ggtgaaacca | aagcactgaa | cagcccatgc | 120 |
| gtcatttcca | catgctatgc | agctgaccgt | aaagtgaact | cgactctctg | cccgaacttc | 180 |
| ggagttgcgg | agggctgcca | tgtggagtgg | acccccgatg | gtgaataccc | gaactgctgc | 240 |
| ccgaagcatg | tgtgccctac | ggcccctgtt | acttcttaat | cgcatcacat | ctgcgaaaat | 300 |

-continued

```
gaaacgtcga gacattcttc tttatgcctt aagaaattaa actgcaacgt ccgcaaaaat    360
acatccccgc ttcaaatacg aacaaaatgc aggatcaaat gctattaggt ttcatgctga    420

<210> SEQ ID NO 6
<211> LENGTH: 92
<212> TYPE: PRT
<213> ORGANISM: Rhipicephalus sanguineus

<400> SEQUENCE: 6

Asp Val Gln Glu Arg Gly His Thr Tyr Val Thr Lys Asn Val Thr Val
1               5                   10                  15

Glu Asn Gly Ala Cys Val Phe Glu Arg Asn Val Ile Pro Asp Gly Glu
            20                  25                  30

Thr Lys Ala Leu Asn Ser Pro Cys Val Ile Ser Thr Cys Tyr Ala Ala
        35                  40                  45

Asp Arg Lys Val Asn Ser Thr Leu Cys Pro Asn Phe Gly Val Ala Glu
    50                  55                  60

Gly Cys His Val Glu Trp Thr Pro Asp Gly Glu Tyr Pro Asn Cys Cys
65                  70                  75                  80

Pro Lys His Val Cys Pro Thr Ala Pro Val Thr Ser
                85                  90

<210> SEQ ID NO 7
<211> LENGTH: 515
<212> TYPE: DNA
<213> ORGANISM: Amblyomma variegatum

<400> SEQUENCE: 7
gttgagctag tgcaagctca cttttacgtc ctgcttcggg gcaagatcac acacccaaaa     60
tgcgtgcgct cgttgcttta gcctgtgtcg tagtcagtgt tgcggtagtc atcggcgaca    120
tccaggaaca tggccactcc tacttgaaga ggaatgtgac tatagagaac ggtgcctgca    180
tctatgagcg caacacactt cctgatggtg aaaccaaggc actccacgac ccctgcgtca    240
ttgcaacctg ctacgctgaa aggcgcgaag tgaatgccac cctgtgccca aacttcggtg    300
tggatcctgg ttgtagggtg cagtggaccc ccgacggcat ctatccagaa tgctgcccga    360
aacaagtgtg cgatggcaca aactgagtcg aatgcatctc ttttgcaaat gcctgtttcg    420
agctgccacg tccaaataca ctgatgactc caagttactc agccggaaaa ttcactttcc    480
gtaaacaggt ttaagattca ataaacattt ctgaa                               515

<210> SEQ ID NO 8
<211> LENGTH: 108
<212> TYPE: PRT
<213> ORGANISM: Amblyomma variegatum

<400> SEQUENCE: 8

Met Arg Ala Leu Val Ala Leu Ala Cys Val Val Val Ser Val Ala Val
1               5                   10                  15

Val Ile Gly Asp Ile Gln Glu His Gly His Ser Tyr Leu Lys Arg Asn
            20                  25                  30

Val Thr Ile Glu Asn Gly Ala Cys Ile Tyr Glu Arg Asn Thr Leu Pro
        35                  40                  45

Asp Gly Glu Thr Lys Ala Leu His Asp Pro Cys Val Ile Ala Thr Cys
    50                  55                  60

Tyr Ala Glu Arg Arg Glu Val Asn Ala Thr Leu Cys Pro Asn Phe Gly
65                  70                  75                  80
```

-continued

```
Val Asp Pro Gly Cys Arg Val Gln Trp Thr Pro Asp Gly Ile Tyr Pro
            85                  90                  95

Glu Cys Cys Pro Lys Gln Val Cys Asp Gly Thr Asn
            100                 105
```

<210> SEQ ID NO 9
<211> LENGTH: 396
<212> TYPE: DNA
<213> ORGANISM: Ixodes scapularis

<400> SEQUENCE: 9

```
atgaggtcaa tcgttctatg ggctctgatc gccttgggag gtgtgccact tctcatggga    60
gccgctaatc aaagccaccc ttatggagtt tcatttaata acggtacatg tacgtaccga   120
aatataacgc tgagagatgg agactctgaa ccttttcaat acccatgtga atattggaat   180
tgcaatgtta cagcaagaac actaactatt gaggggtgcg gtgttccacg atacggaagt   240
tgcctgtacg tgcacaatta taatttctac tggcctcttt gctgtcgcat gagtcgtctc   300
tgttgaaaca attaactaat ttaccttcac ttctatcaga acactttgct ggtaaataaa   360
aaagaaaac aacaaaaaaa aaaaaaaaaa aaaaaa                              396
```

<210> SEQ ID NO 10
<211> LENGTH: 101
<212> TYPE: PRT
<213> ORGANISM: Ixodes scapularis

<400> SEQUENCE: 10

```
Met Arg Ser Ile Val Leu Trp Ala Leu Ile Ala Leu Gly Gly Val Pro
1                5                  10                  15

Leu Leu Met Gly Ala Ala Asn Gln Ser His Pro Tyr Gly Val Ser Phe
            20                  25                  30

Asn Asn Gly Thr Cys Thr Tyr Arg Asn Ile Thr Leu Arg Asp Gly Asp
            35                  40                  45

Ser Glu Pro Phe Gln Tyr Pro Cys Glu Tyr Trp Asn Cys Asn Val Thr
        50                  55                  60

Ala Arg Thr Leu Thr Ile Glu Gly Cys Gly Val Pro Arg Tyr Gly Ser
65                  70                  75                  80

Cys Leu Tyr Val His Asn Tyr Asn Phe Tyr Trp Pro Leu Cys Cys Arg
                85                  90                  95

Met Ser Arg Leu Cys
            100
```